US009775610B2

(12) United States Patent
Nicholas et al.

(10) Patent No.: US 9,775,610 B2
(45) Date of Patent: Oct. 3, 2017

(54) APPARATUS FOR ENDOSCOPIC PROCEDURES

(71) Applicant: Covidien LP, Mansfield, MA (US)

(72) Inventors: David A. Nicholas, Trumbull, CT (US); Paul A. Scirica, Huntington, CT (US); Justin Williams, Southbury, CT (US); Kevin Slisz, Old Saybrook, CT (US)

(73) Assignee: Covidien LP, Mansfield, MA (US)

( * ) Notice: Subject to any disclaimer, the term of this patent is extended or adjusted under 35 U.S.C. 154(b) by 616 days.

(21) Appl. No.: 14/279,420

(22) Filed: May 16, 2014

(65) Prior Publication Data
US 2014/0303668 A1    Oct. 9, 2014

Related U.S. Application Data

(63) Continuation-in-part of application No. 13/859,066, filed on Apr. 9, 2013.

(51) Int. Cl.
*A61B 17/29* (2006.01)
*A61B 17/28* (2006.01)
(Continued)

(52) U.S. Cl.
CPC ..... *A61B 17/07207* (2013.01); *A61B 2017/0046* (2013.01); *A61B 2017/00389* (2013.01);
(Continued)

(58) Field of Classification Search
CPC .......... A61B 17/2804; A61B 2017/293; A61B 17/068; A61B 17/29; A61B 17/1631; A61B 17/07207; Y10T 16/293
(Continued)

(56) References Cited

U.S. PATENT DOCUMENTS 2,777,340 A    1/1957  Hettwer et al.
2,957,353 A   10/1960  Babacz
(Continued)

FOREIGN PATENT DOCUMENTS

AU    2008229795 A1    4/2009
CA      2451558 A1    1/2003
(Continued)

OTHER PUBLICATIONS

Supplemental Partial European Search Report dated Dec. 14, 2015, issued in EP Application No. 15167793.
(Continued)

*Primary Examiner* — Hemant M Desai
*Assistant Examiner* — Lucas Palmer

(57) ABSTRACT

A surgical device includes a jaw assembly, an articulating assembly and a drive shaft. The jaw assembly includes first and second jaws. The articulating assembly is removably coupled to a proximal end of the jaw assembly and includes a distal joint member, a proximal joint member, and a pivot pin. The pivot pin is fixedly coupled to the distal joint member and is rotatably coupled to the proximal joint member. The jaw assembly and the distal joint member together define a first longitudinal axis. The proximal joint member defines a second longitudinal axis. The drive shaft includes a gear element that is meshingly engaged with a pivoting gear element that is fixedly coupled to the pivot pin. Longitudinal movement of the first drive shaft pivots the jaw assembly relative to the proximal joint member about a pivot axis defined by the pivot pin.

19 Claims, 24 Drawing Sheets

(51) Int. Cl.
*A61B 17/072* (2006.01)
*A61B 17/00* (2006.01)

(52) U.S. Cl.
CPC ........... *A61B 2017/00398* (2013.01); *A61B 2017/00473* (2013.01); *A61B 2017/00734* (2013.01); *A61B 2017/2927* (2013.01)

(58) Field of Classification Search
USPC .................................................... 227/175.2
See application file for complete search history.

(56) References Cited

U.S. PATENT DOCUMENTS

| | | | |
|---|---|---|---|
| 3,111,328 A | 11/1963 | Di Rito et al. | |
| 3,256,875 A * | 6/1966 | Tsepelev | A61B 1/00163 359/737 |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,471,781 A * | 9/1984 | Di Giovanni | A61B 17/0491 606/145 |
| 4,606,343 A | 8/1986 | Conta et al. | |
| 4,705,038 A | 11/1987 | Sjostrom et al. | |
| 4,722,685 A | 2/1988 | de Estrada et al. | |
| 4,752,024 A * | 6/1988 | Green | A61B 17/115 227/19 |
| 4,771,781 A | 9/1988 | Lerman | |
| 4,823,807 A | 4/1989 | Russell et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,403,327 A * | 4/1995 | Thornton | A61B 17/1285 227/91 |
| 5,411,508 A | 5/1995 | Bessler et al. | |
| 5,413,267 A | 5/1995 | Solyntjes et al. | |
| 5,427,087 A | 6/1995 | Ito et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,632,432 A | 5/1997 | Schulze et al. | |
| 5,647,526 A | 7/1997 | Green et al. | |
| 5,653,374 A | 8/1997 | Young et al. | |
| 5,658,300 A | 8/1997 | Bito et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A * | 7/1998 | Mastri | A61B 17/07207 227/175.3 |
| 5,782,397 A | 7/1998 | Koukline | |
| 5,797,536 A | 8/1998 | Smith et al. | |
| 5,820,009 A | 10/1998 | Melling et al. | |
| 5,863,159 A | 1/1999 | Lasko | |
| 5,865,361 A | 2/1999 | Milliman et al. | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A * | 11/1999 | Longo | A61B 17/1624 606/80 |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 * | 6/2001 | Milliman | A61B 17/07207 227/175.1 |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 7,032,798 B2 | 4/2006 | Whitman et al. | |
| RE39,152 E | 6/2006 | Aust et al. | |
| 7,055,731 B2 | 6/2006 | Shelton, IV et al. | |
| 7,059,508 B2 | 6/2006 | Shelton, IV et al. | |
| 7,077,856 B2 | 7/2006 | Whitman | |
| 7,111,769 B2 | 9/2006 | Wales et al. | |
| 7,122,029 B2 | 10/2006 | Koop et al. | |
| 7,140,528 B2 | 11/2006 | Shelton, IV | |
| 7,143,923 B2 | 12/2006 | Shelton, IV et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,172,104 B2 | 2/2007 | Scirica et al. | |
| 7,225,964 B2 | 6/2007 | Mastri et al. | |
| 7,238,021 B1 | 7/2007 | Johnson | |

(56) References Cited

U.S. PATENT DOCUMENTS

| | | |
|---|---|---|
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 * | 7/2008 | Smith .............. A61B 17/07207 227/175.1 |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 * | 6/2009 | Boudreaux ...... A61B 17/07207 227/175.1 |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 * | 4/2011 | Whitman .......... A61B 17/07207 128/898 |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 * | 9/2011 | Whitman .............. A61B 17/072 227/175.1 |
| 8,020,743 B2 * | 9/2011 | Shelton, IV ..... A61B 17/07207 227/175.1 |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0143346 A1 | 10/2002 | McGuckin et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0025809 A1 * | 2/2006 | Shelton, IV ..... A61B 17/07207 606/205 |
| 2006/0025817 A1 * | 2/2006 | Ortiz ................ A61B 17/07207 606/219 |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0226196 A1 * | 10/2006 | Hueil ................ A61B 17/07207 227/175.1 |
| 2006/0259073 A1 | 11/2006 | Miyamoto et al. |

(56) References Cited

U.S. PATENT DOCUMENTS

| | | |
|---|---|---|
| 2006/0278680 A1 | 12/2006 | Viola et al. |
| 2007/0023476 A1* | 2/2007 | Whitman ............ A61B 17/072 227/175.1 |
| 2007/0023477 A1* | 2/2007 | Whitman ......... A61B 17/07207 227/175.1 |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1* | 8/2007 | Shelton, IV ..... A61B 17/07207 227/178.1 |
| 2007/0175964 A1* | 8/2007 | Shelton, IV ......... A61B 17/072 227/180.1 |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237015 A1* | 10/2008 | Rakus ................ H01H 71/1009 200/400 |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1* | 10/2008 | Omori .................... A61B 90/96 700/245 |
| 2008/0308603 A1 | 12/2008 | Shelton et al. |
| 2009/0090763 A1 | 4/2009 | Zemlok et al. |
| 2009/0090764 A1* | 4/2009 | Viola ............... A61B 17/07207 227/176.1 |
| 2009/0099876 A1 | 4/2009 | Whitman |
| 2009/0101692 A1* | 4/2009 | Whitman ......... A61B 17/07207 227/175.1 |
| 2009/0108048 A1* | 4/2009 | Zemlok ............ A61B 17/07207 227/175.1 |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0206130 A1* | 8/2009 | Hall ................. A61B 17/07207 227/175.2 |
| 2009/0206131 A1* | 8/2009 | Weisenburgh, II ..................... A61B 17/07207 227/175.2 |
| 2009/0209990 A1 | 8/2009 | Yates et al. |
| 2009/0254094 A1 | 10/2009 | Knapp et al. |
| 2010/0010512 A1* | 1/2010 | Taylor .................... A61B 17/04 606/144 |
| 2010/0069942 A1 | 3/2010 | Shelton, IV |
| 2010/0193568 A1* | 8/2010 | Scheib ............. A61B 17/07207 227/176.1 |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1* | 8/2011 | McCuen .......... A61B 17/07207 227/175.1 |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0296169 A1* | 11/2012 | Kleyman ............. A61B 1/3132 600/204 |
| 2012/0310220 A1* | 12/2012 | Malkowski ............ A61B 17/29 606/1 |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0206814 A1* | 8/2013 | Morgan ........... A61B 17/07207 227/176.1 |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0312563 A1* | 11/2013 | Kawashima ............. B25J 18/02 74/490.01 |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1* | 12/2013 | Williams ............. A61B 17/068 227/176.1 |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0144970 A1 | 5/2014 | Aranyi et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0243801 A1* | 8/2014 | Fanelli ............. A61B 17/07207 606/1 |
| 2014/0246476 A1* | 9/2014 | Hall .................... A61B 17/068 227/175.1 |
| 2014/0246479 A1* | 9/2014 | Baber .................. A61B 17/068 227/180.1 |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1* | 12/2014 | Zergiebel ................. F16H 19/02 74/89.23 |
| 2015/0048144 A1 | 2/2015 | Whitman |
| 2015/0076205 A1* | 3/2015 | Zergiebel ......... A61B 17/07207 227/175.1 |
| 2015/0080912 A1 | 3/2015 | Sapre |

(56) References Cited

U.S. PATENT DOCUMENTS

| | | | |
|---|---|---|---|
| 2015/0122870 A1* | 5/2015 | Zemlok | H02P 7/29 227/176.1 |
| 2015/0157321 A1 | 6/2015 | Zergiebel et al. | |
| 2015/0164502 A1 | 6/2015 | Richard et al. | |
| 2015/0272577 A1 | 10/2015 | Zemlok et al. | |
| 2015/0297199 A1 | 10/2015 | Nicholas et al. | |
| 2015/0303996 A1 | 10/2015 | Calderoni | |
| 2015/0320420 A1 | 11/2015 | Penna et al. | |
| 2015/0327850 A1 | 11/2015 | Kostrzewski | |
| 2015/0342601 A1 | 12/2015 | Williams et al. | |
| 2015/0342603 A1 | 12/2015 | Zergiebel et al. | |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0095585 A1 | 4/2016 | Zergiebel et al. | |
| 2016/0095596 A1 | 4/2016 | Scirica et al. | |
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |

FOREIGN PATENT DOCUMENTS

| | | | |
|---|---|---|---|
| CN | 101856251 A | 10/2010 | |
| CN | 102247182 A | 11/2011 | |
| DE | 102008053842 A1 | 5/2010 | |
| EP | 0634144 A1 | 1/1995 | |
| EP | 0648476 A1 | 4/1995 | |
| EP | 0686374 A2 | 12/1995 | |
| EP | 0705571 A1 | 4/1996 | |
| EP | 1690502 A1 | 8/2006 | |
| EP | 1723913 A1 | 11/2006 | |
| EP | 1736112 A1 | 12/2006 | |
| EP | 1759652 A2 | 3/2007 | |
| EP | 1769754 A1 | 4/2007 | |
| EP | 1772105 A1 | 4/2007 | |
| EP | 1 813 203 A2 | 8/2007 | |
| EP | 1813199 A1 | 8/2007 | |
| EP | 1813211 A2 | 8/2007 | |
| EP | 1908412 A2 | 4/2008 | |
| EP | 1917929 A1 | 5/2008 | |
| EP | 1943954 A2 | 7/2008 | |
| EP | 1943956 A2 | 7/2008 | |
| EP | 1943958 A1 | 7/2008 | |
| EP | 1943976 A2 | 7/2008 | |
| EP | 1952769 A2 | 8/2008 | |
| EP | 2005898 A2 | 12/2008 | |
| EP | 2027819 A1 | 2/2009 | |
| EP | 2044890 A1 | 4/2009 | |
| EP | 2055243 A2 | 5/2009 | |
| EP | 2090247 A1 | 8/2009 | |
| EP | 2098170 A2 | 9/2009 | |
| EP | 2100561 A2 | 9/2009 | |
| EP | 2100562 A2 | 9/2009 | |
| EP | 2165664 A2 | 3/2010 | |
| EP | 2236098 A2 | 10/2010 | |
| EP | 2245994 A1 | 11/2010 | |
| EP | 2263568 A2 | 12/2010 | |
| EP | 2272443 A1 | 1/2011 | |
| EP | 2316345 A1 | 5/2011 | |
| EP | 2324776 A2 | 5/2011 | |
| EP | 2329773 A1 | 6/2011 | |
| EP | 2333509 A1 | 6/2011 | |
| EP | 2377472 A1 | 10/2011 | |
| EP | 2412319 A2 * | 2/2012 | A61B 17/1285 |
| EP | 2462878 A1 | 6/2012 | |
| EP | 2462880 A2 | 6/2012 | |
| EP | 2491872 A1 | 8/2012 | |
| EP | 2586382 A2 * | 5/2013 | A61B 17/07207 |
| EP | 2606834 A2 | 6/2013 | |
| EP | 2668910 A2 | 12/2013 | |
| EP | 2676615 A2 | 12/2013 | |
| EP | 2815705 A1 | 12/2014 | |
| ES | 2333509 A1 | 2/2010 | |
| FR | 2861574 A1 | 5/2005 | |
| IL | WO 2011092692 A2 * | 8/2011 | A61B 17/068 |
| JP | 08-038488 | 2/1996 | |
| JP | 2005-125075 A | 5/2005 | |
| KR | 20120022521 A | 3/2012 | |
| WO | 99/15086 A1 | 4/1999 | |
| WO | 00/72760 A1 | 12/2000 | |
| WO | 00/72765 A1 | 12/2000 | |
| WO | 03/000138 A2 | 1/2003 | |
| WO | 03/026511 A1 | 4/2003 | |
| WO | 03/030743 A2 | 4/2003 | |
| WO | 03065916 A1 | 8/2003 | |
| WO | 03/077769 A1 | 9/2003 | |
| WO | 03090630 A2 | 11/2003 | |
| WO | 2004/107989 A1 | 12/2004 | |
| WO | 2006/042210 A2 | 4/2006 | |
| WO | 2007016290 A2 | 2/2007 | |
| WO | 2007/026354 A1 | 3/2007 | |
| WO | 2007137304 A2 | 11/2007 | |
| WO | 2008/131362 A2 | 10/2008 | |
| WO | 2008/133956 A2 | 11/2008 | |
| WO | 2009039506 A1 | 3/2009 | |
| WO | 2007014355 A3 | 4/2009 | |
| WO | 2009/132359 A2 | 10/2009 | |
| WO | 2009/143092 A1 | 11/2009 | |
| WO | 2009149234 A1 | 12/2009 | |
| WO | 2011092692 A2 | 8/2011 | |
| WO | 2011/108840 A2 | 9/2011 | |
| WO | 2012040984 A1 | 4/2012 | |

OTHER PUBLICATIONS

Extended European Search Report corresponding to International Application No. EP 15 15 1076.5 dated Apr. 22, 2015.

Japanese Office Action corresponding to International Application No. JP 2011-084092 dated Jan. 14, 2016.

Extended European Search Report corresponding to International Application No. EP 12 19 7970.2 dated Jan. 28, 2016.

Chinese Office Action corresponding to International Application No. CN 201210560638.1 dated Oct. 21, 2015.

European Office Action corresponding to International Application No. EP 14 15 9056.2 dated Oct. 26, 2015.

Australian Examination Report No. 1 corresponding to International Application No. AU 2015200153 dated Dec. 11, 2015.

Australian Examination Report No. 1 corresponding to International Application No. AU 2014204542 dated Jan. 7, 2016.

Chinese Office Action corresponding to International Application No. CN 201310125449.6 dated Feb. 3, 2016.

Extended European Search Report corresponding to International Application No. EP 15 19 0245.9 dated Jan. 28, 2016.

Extended European Search Report corresponding to International Application No. EP 15 16 7793.7 dated Apr. 5, 2016.

European Office Action corresponding to International Application No. EP 14 18 4882.0 dated Apr. 25, 2016.

Extended European Search Report corresponding to International Application No. EP 14 19 6704.2 dated Sep. 24, 2015.

International Search Report and Written Opinion corresponding to Int'l Appln. No. PCT/US2015/051837, mailed Dec. 21, 2015.

Extended European Search Report corresponding to International Application No. EP 14 19 7563.1 dated Aug. 5, 2015.

Partial European Search Report corresponding to International Application No. EP 15 19 0643.5 dated Feb. 26, 2016.

Extended European Search Report corresponding to International Application No. EP 15 16 6899.3 dated Feb. 3, 2016.

Extended European Search Report corresponding to International Application No. EP 14 19 9783.3 dated Dec. 22, 2015.

Extended European Search Report corresponding to International Application No. EP 15 17 3807.7 dated Nov. 24, 2015.

Extended European Search Report corresponding to International Application No. EP 15 19 0760.7 dated Apr. 1, 2016.

Extended European Search Report corresponding to International Application No. EP 15 17 3803.6 dated Nov. 24, 2015.

(56) References Cited

OTHER PUBLICATIONS

Extended European Search Report corresponding to International Application No. EP 15 17 3804.4 dated Nov. 24, 2015.
Extended European Search Report corresponding to International Application No. EP 15 18 8539.9 dated Feb. 17 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
International Search Report corresponding to PCT/US2005/027266, completed May 30, 2008 and mailed Jun. 18, 2008; (2 pp.).
Extended European Search Report corresponding to EP 08 25 2703.7, completed Oct. 23, 2008 and mailed Oct. 31, 2008; (7 pp.).
Extended European Search Report corresponding to EP 08 25 3184.9, completed Feb. 12, 2009 and mailed Feb. 27, 2009; (3 pp.).
Extended European Search Report corresponding to EP 10 25 0228.3, completed May 20, 2010 and mailed Jun. 1, 2010; (6 pp.).
Extended European Search Report corresponding to EP 10 25 2037.6, completed Mar. 1, 2011 and mailed Mar. 9, 2011; (3 pp.).
Extended European Search Report corresponding to EP 10 25 1968.3, completed on Jul. 4, 2011 and mailed Jul. 14, 2011; (12 pp.).
Extended European Search Report corresponding to EP 11 15 2266.0, completed Jul. 15, 2011 and mailed Jul. 28, 2011; (3 pp.).
Extended European Search Report corresponding to EP 11 25 0462.6, completed Jul. 20, 2011 and mailed Jul. 28, 2011; (6 pp.).
Extended European Search Report corresponding to EP 11 25 0771.0, completed Feb. 7, 2012 and mailed Feb. 17, 2012; (3 pp.).
Extended European Search Report corresponding to EP 06 78 8914.7, completed May 3, 2012 and mailed May 11, 2012; (8 pp.).
Partial European Search Report corresponding to EP 12 18 6177.7, completed Jan. 30, 2013 and mailed Feb. 12, 2013; (6 pp.).
Extended European Search Report corresponding to EP No. 11 17 8021.9, mailed Jun. 4, 2013; (3 pp).
Extended European Search Report corresponding to EP No. 13 16 3033.7, completed Jun. 27, 2013 and mailed Jul. 15, 2013; (8 pp).
Extended European Search Report corresponding to EP No. 12 18 6177.7, completed Aug. 14, 2013 and mailed Aug. 23, 2013; (8 pp).
Partial European Search Report corresponding to EP No. 13 17 1742.3, completed Sep. 17, 2013 and mailed Sep. 25, 2013; (8 pp).
Partial European Search Report corresponding to EP No. 13 17 2400.7, completed Sep. 18, 2013 and mailed Oct. 1, 2013; (7 pp).
Extended European Search Report corresponding to EP No. 13 17 5475.6, completed Sep. 23, 2013 and mailed Oct. 1, 2013; (8 pp).
Extended European Search Report corresponding to EP No. 13 17 5478.0, completed Sep. 24, 2013 and mailed Oct. 2, 2013; (6 pp).
Extended European Search Report corresponding to EP No. 13 17 5479.8, completed Sep. 27, 2013 and mailed Oct. 10, 2013; (7 pp).
Partial Extended European Search Report corresponding to EP 13 17 5477.2, completed Oct. 7, 2013 and mailed Oct. 15, 2013; (7 pp).
Extended European Search Report corresponding to EP No. 08 25 2703.7, completed Oct. 23, 2008 and mailed Oct. 31, 2008; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
Extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
Extended European Search Report corresponding to Application No. EP 14152236.7 mailed May 12, 2014.
Partial European Search Report from Application No. EP 14159056.2 dated Jun. 18, 2014 (8 pp).
European Search Report dated Apr. 5, 2016, issued in European Appln No. 15167793.
European Search Report dated Nov. 25, 2016, issued in EP Application No. 14163804.

* cited by examiner

APPARATUS FOR ENDOSCOPIC PROCEDURES

CROSS REFERENCE TO RELATED APPLICATIONS

The present application is a continuation-in-part application of U.S. patent application Ser. No. 13/859,066 filed on Apr. 9, 2013, the entire disclosure of which is incorporated by reference herein.

BACKGROUND

1. Technical Field

The present disclosure relates to surgical apparatus, devices and/or systems for performing endoscopic surgical procedures and methods of use thereof. More specifically, the present disclosure relates to electromechanical, robotic and/or hand-held surgical apparatus, devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating electromechanical surgical devices. In many instances the electromechanical surgical devices include a handle assembly, which is reusable, and disposable loading units and/or single use loading units or the like that are selectively connected to the handle assembly prior to use and then disconnected from the handle assembly following use in order to be disposed of or in some instances sterilized for re-use.

Various electromechanical linkages are utilized to transmit power from the reusable handle assemblies, which include one or more motors, to the disposable loading unit to effect rotation, pivoting, clamping, fastener ejection, etc. Due to the complex structure and operation of the power transmission mechanisms inadvertent actuation of these mechanisms may result in unintended operation of the disposable loading unit, which may result in damage to the surgical device and/or injury to the patient. Robotic systems for performing minimally invasive surgery are also known. For example, International Application Publication WO 2000/051486 discloses a system having remotely-controlled surgical instruments.

Many of these electromechanical surgical devices are relatively expensive to manufacture, purchase and/or operate. There is a constant desire by manufacturers and end users to develop electromechanical surgical devices that are relatively inexpensive to manufacture, purchase and/or operate that still provide a large degree of operability with prerequisite safety features. Accordingly, a need exists for electromechanical surgical apparatus, devices and/or systems that include effective electromechanical transmission system for actuating the disposable units as well as safety lockout assemblies.

SUMMARY

According to an aspect of the present disclosure, a surgical device includes a jaw assembly, an articulating assembly and a drive shaft. The jaw assembly includes a first jaw and a second jaw moveable relative to the first jaw. The articulating assembly is removably coupled to a proximal end of the jaw assembly and includes a distal joint member, a proximal joint member, and a pivot pin. The pivot pin is fixedly coupled to the distal joint member and is rotatably coupled to the proximal joint member. The jaw assembly and the distal joint member together define a first longitudinal axis extending between the proximal end of the jaw assembly and a distal end of the distal joint member. The proximal joint member defines a second longitudinal axis. The drive shaft includes a gear element that is meshingly engaged with a pivoting gear element. The pivoting gear element is fixedly coupled to the pivot pin. Longitudinal movement of the first drive shaft pivots the jaw assembly relative to the proximal joint member about a pivot axis defined by the pivot pin. The pivot axis is perpendicular to the first and second longitudinal axes.

In aspects, the gear element is a toothed rack and the pivoting gear element is a pinion drive.

In some aspects, the surgical device includes an elongated member that is coupled to the proximal joint member. The elongated member may include a drive shaft. In certain aspects, the device includes a handle assembly that is removably coupled to a proximal end of the elongated member. The handle assembly may include a motor mechanically coupled to the drive shaft. The motor may be configured to longitudinally move the drive shaft. The drive shaft may be configured to apply a force that back drives the motor in response to an external force applied to the articulating assembly about the pivot axis.

In aspects, the drive shaft includes a proximal stop, a distal stop, and a thrust plate positioned between the proximal and distal stops. The proximal stop may be positioned along the first drive shaft at a first position corresponding to a first pivoted position of the distal joint member and the distal stop may be positioned along the first drive shaft at a second position corresponding to a second pivoted position of the distal joint member. In the first pivoted position, the second longitudinal axis may define a first angle with the first longitudinal axis in a first direction. In the second pivoted position, the second longitudinal axis may define a second angle with the first longitudinal axis in a second direction. The second direction may be opposite the first direction. The first and second angles may be about 150°. Alternatively, the first and second angles may be about 90°.

In another aspect of the present disclosure, a surgical device includes a jaw assembly, an articulating neck assembly, a first drive shaft, a second drive shaft, and a third drive shaft. The jaw assembly includes a first jaw and a second jaw moveable relative to the first jaw. The articulating neck assembly is removably coupled to the proximal end of the jaw assembly and includes a distal joint member, a proximal joint member, and a pivot pin. The pivot pin is fixedly coupled to the distal joint member and is rotatably coupled to the proximal joint member. The jaw assembly and the distal joint member define a first longitudinal axis that extends between a proximal end of the jaw assembly and a distal end of the distal joint member. The proximal joint member defines a second longitudinal axis. The first drive shaft is coupled to the pivot pin. Longitudinal movement of the first drive shaft pivots the jaw assembly relative to the proximal joint member about a pivot axis defined by the pivot pin. The pivot axis is perpendicular to the first and second longitudinal axes. The second drive shaft is coupled to the jaw assembly. Rotation of the second drive shaft moves the second jaw relative to the first jaw. The third drive shaft is coupled to the jaw assembly. Rotation of the third drive shaft rotates the jaw assembly about the first longitudinal axis.

In aspects, the first drive shaft includes a first gear element that is meshingly engaged with a pivoting gear element. The pivoting gear element may be fixedly coupled to the pivot pin. The first gear element may be a toothed rack and the pivoting gear element may be a pinion drive.

In some aspects, the surgical device includes an elongated member coupled to the proximal joint member. The proximal joint member may include the first drive shaft. The surgical device may include a handle assembly that is removably coupled to a proximal end of the elongated member. The handle assembly may include a motor mechanically coupled to the first drive shaft. The motor may be configured to longitudinally move the first drive shaft. The first drive shaft may apply a force that back drives the motor when an external force is applied to the articulating assembly about the pivot axis. The first drive shaft may include a proximal stop, a distal stop and a thrust plate positioned between the proximal and distal stops. The proximal stop may be positioned along the first drive shaft at a first position corresponding to a first pivoted position of the distal joint member. The distal stop may be positioned along the first drive shaft at a second position corresponding to a second pivoted position of the distal joint member. In the first pivoted position, the second longitudinal axis may define a first angle with the first longitudinal axis in a first direction. In the second pivoted position, the second longitudinal axis may define a second angle with the first longitudinal axis in a second direction. The second direction may be opposite the first direction.

Further details and aspects of exemplary embodiments of the present invention are described in more detail below with reference to the appended figures.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
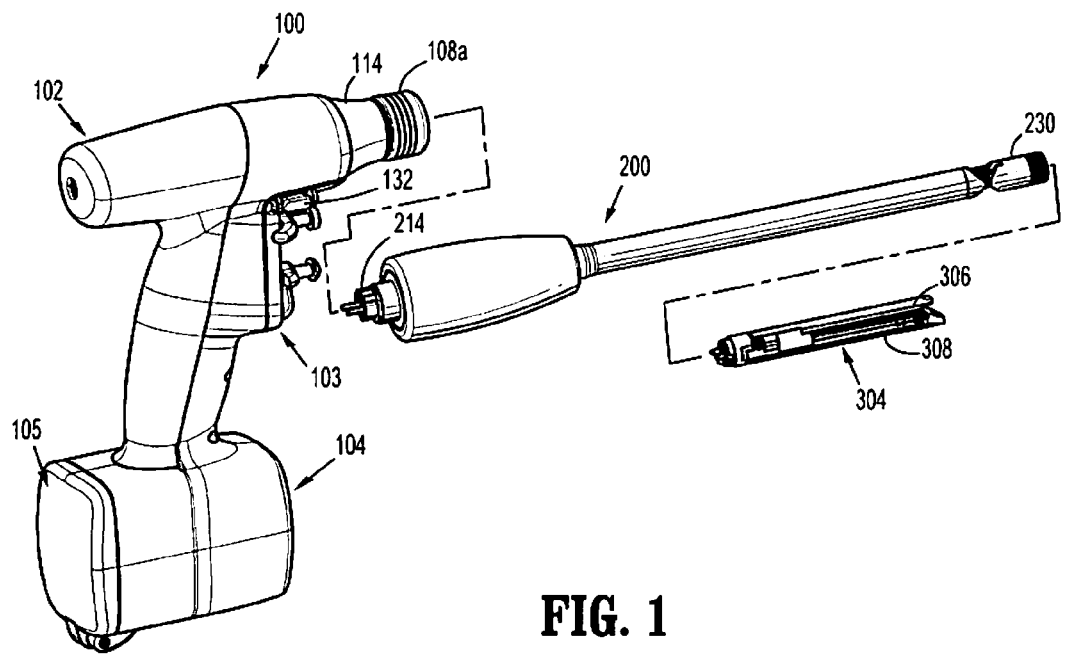
FIG. 1 is a perspective, disassembled view of an electromechanical surgical system including a surgical instrument, an adapter assembly, and an end effector, according to the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user. The terms "left" and "right" refer to that portion of the electromechanical surgical system, apparatus and/or device, or component thereof, that are on the left and right sides, respectively, from the perspective of the user facing the distal end of the electromechanical surgical system, apparatus and/or device from the proximal end while the surgical system, apparatus and/or device is oriented in non-rotational configuration.

Reference may be made to International Application Publication No. WO 2009/039506 and U.S. Patent Application Publication US 2011/0121049, the entire contents of each of which are incorporated by reference herein, for a detailed description of the construction and operation of exemplary electromechanical, hand-held, powered surgical instrument 100.

Referring initially to FIGS. 1-8, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment thereto of a plurality of different end effectors 300, via an adapter assembly (e.g., elongated body) 200. The end effector 300 and the adapter assembly 200 are configured for actuation and manipulation by the electromechanical, hand-held, powered surgical instrument 100. In particular, the surgical instrument 100, the adapter assembly 200, and the end effector 300 are separable from each other such that the surgical instrument 100 is configured for selective connection with adapter assembly 200, and, in turn, adapter assembly 200 is configured for selective connection with any one of a plurality of different end effectors 300.

The end effector and/or adapter can be configured as an integral unit in any of the embodiments disclosed herein. The end effector and/or adapter can be configured for use with a powered handle, console, and/or surgical robot, in any of the embodiments disclosed herein.

Figure 2:
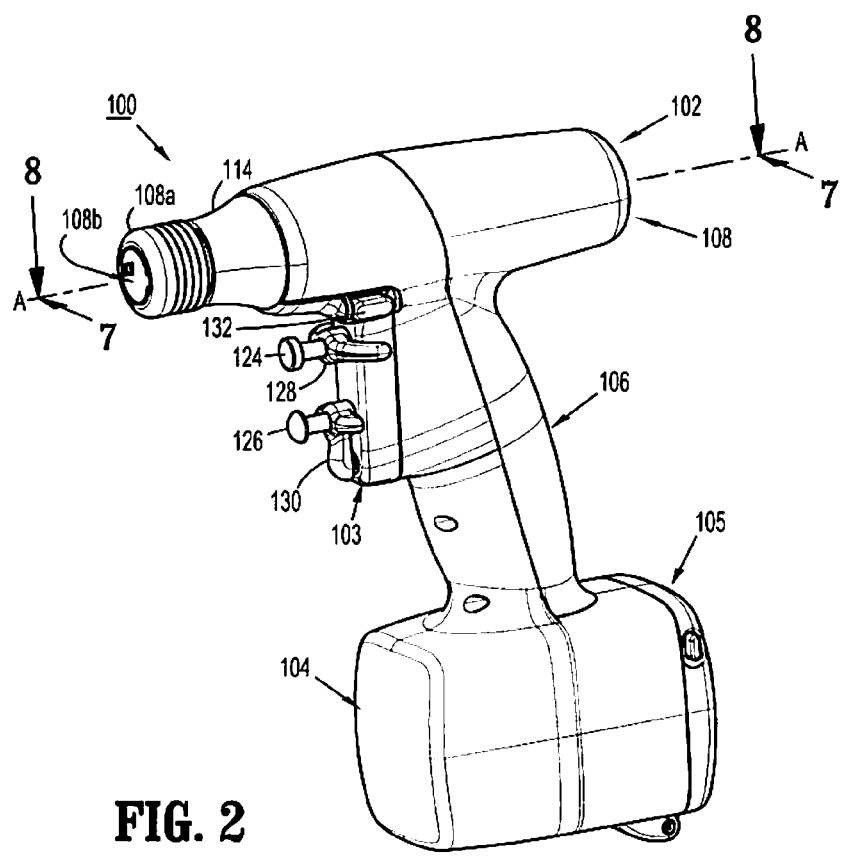
FIG. 2 is a perspective view of the surgical instrument of FIG. 1, according to the present disclosure.
Figure 3:
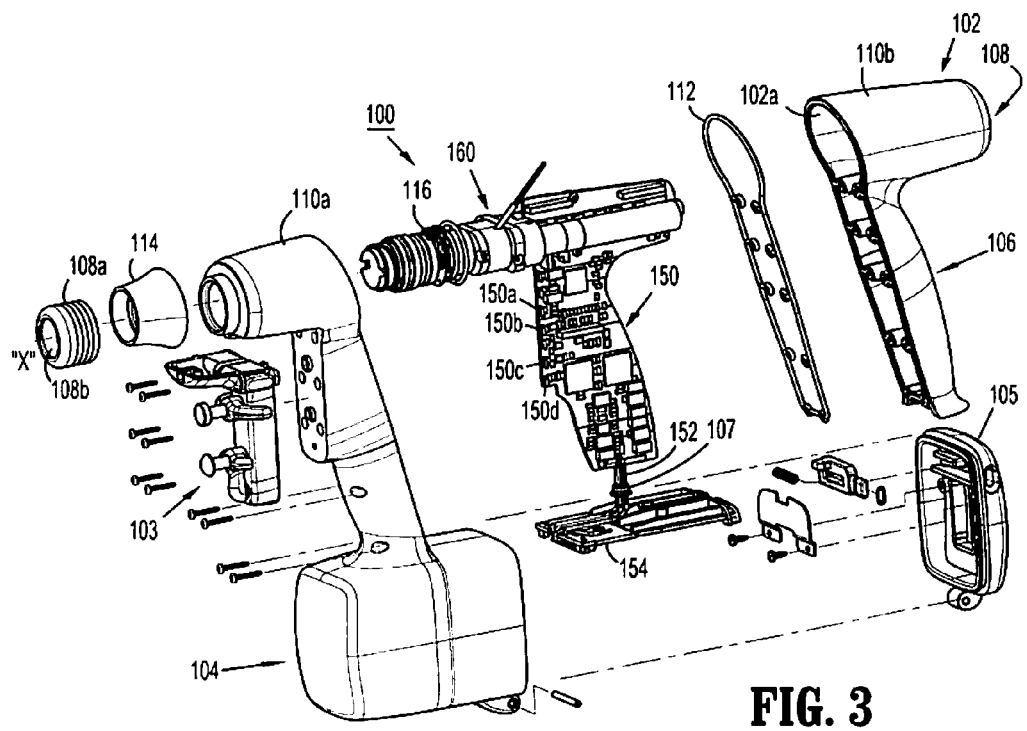
FIG. 3 is perspective, disassembled view of the surgical instrument of FIG. 1, according to the present disclosure.

As illustrated in FIGS. 1-3, the hand-held surgical instrument 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 are situated.

With reference to FIGS. 2 and 3, distal and proximal half-sections 110a, 110b are divided along a vertical plane that traverses a longitudinal axis "A-A" of upper housing portion 108 (FIG. 2). Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical instrument 100, as will be set forth in additional detail below.

Figure 4:
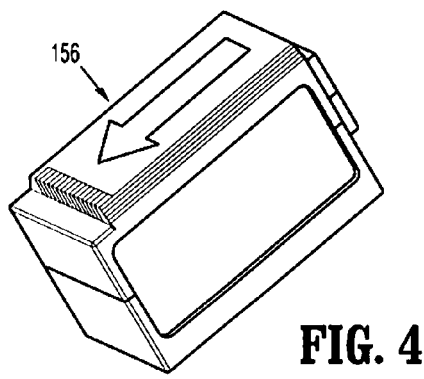
FIG. 4 is a perspective view of a battery of the surgical instrument of FIG. 1, according to the present disclosure.

Lower housing portion 104 of surgical instrument 100 defines an aperture (not shown) formed in an upper surface thereof and which is located beneath or within intermediate housing portion 106. As shown in FIGS. 3 and 4, the aperture of lower housing portion 104 provides a passage through which wires 152 pass to electrically interconnect electrical components situated in lower housing portion 104, e.g., a battery 156 and a circuit board 154, with electrical components situated in intermediate housing portion 106 and/or upper housing portion 108, e.g., circuit board 150, drive mechanism 160, etc.

Handle housing 102 includes a gasket 107 disposed within the aperture of lower housing portion 104 thereby plugging or sealing the aperture of lower housing portion 104 while allowing wires 152 to pass therethrough (see FIG. 3). Gasket 107 functions to establish an air-tight seal between lower housing portion 106 and intermediate housing portion 108 such that circuit board 150 and drive mechanism 160 are protected from sterilization and/or cleaning procedures.

With continued reference to FIGS. 3 and 4, lower housing portion 104 of handle housing 102 provides a housing in which the battery 156 is removably disposed therein. The battery 156 may be a rechargeable battery (e.g., lead-based, nickel-based, lithium-ion based, etc.). It is also envisioned that the battery 156 may be a single-use, non-rechargeable battery. Battery 156 is configured to supply power to any of the electrical components of surgical instrument 100. Lower housing portion 104 defines a cavity (not shown) into which battery 156 is inserted. Lower housing portion 104 includes a door 105 pivotally connected thereto for closing cavity of lower housing portion 104 and retaining battery 156 therein.

Figure 5:
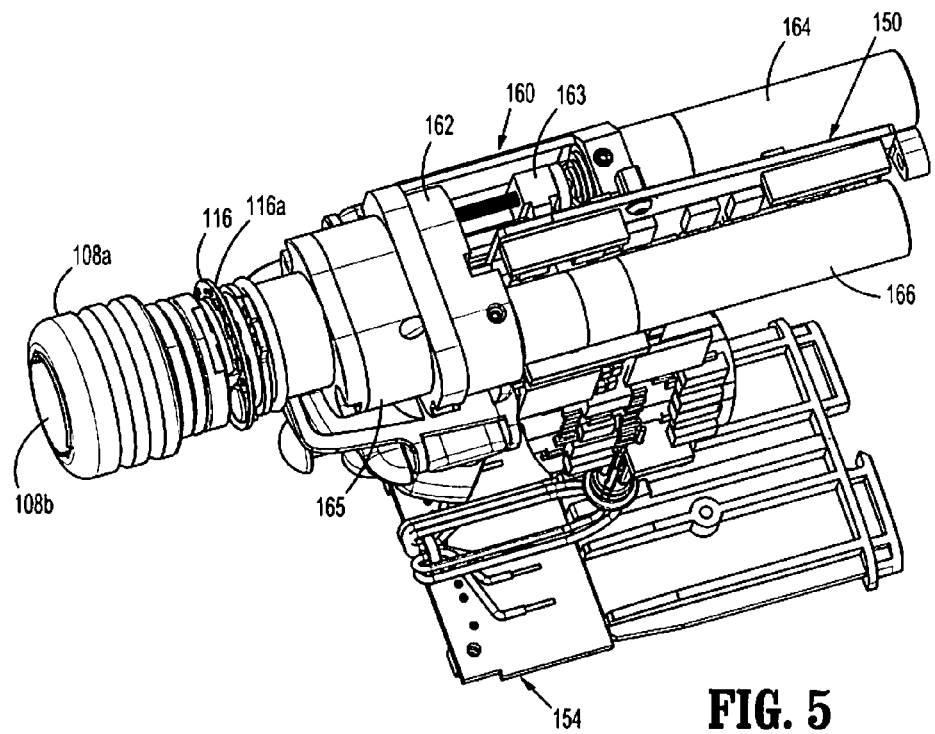
FIG. 5 is a top, partially-disassembled view of the surgical instrument of FIG. 1, according to the present disclosure.

With continued reference to FIGS. 3 and 5, distal half-section 110a of upper housing portion 108 defines a nose or connecting portion 108a. A nose cone 114 is supported on nose portion 108a of upper housing portion 108. Nose cone 114 is fabricated from a transparent, light-transmissive material. An illumination member 116 is disposed within nose cone 114 such that illumination member 116 is visible therethrough. The nose cone 114 may be tinted, such that the illumination member 116 is visible when it is activated.

With reference to FIG. 5, the illumination member 116 may include a plurality of any suitable light emitting devices, such as light emitting diodes (LEDs), disposed on printed circuit board (LED PCB) 116a which is disposed in a vertical plane transverse to the longitudinal axis "A-A." The illumination member 116 is configured to illuminate in multiple colors with a specific color pattern being associated with a unique discrete event. In embodiments, the LEDs may be single-color or multi-color LEDs.

Upper housing portion 108 of handle housing 102 provides a housing in which drive mechanism 160 is situated. As illustrated in FIG. 5, drive mechanism 160 is configured to drive shafts and/or gear components in order to perform the various operations of surgical instrument 100. In particular, drive mechanism 160 is configured to drive shafts and/or gear components in order to selectively move tool assembly 304 of end effector 300 relative to the adapter assembly, to rotate end effector 300 about the longitudinal axis "A-A" (FIG. 2) relative to handle housing 102, to move anvil assembly 306 relative to cartridge assembly 308 of end effector 300, and/or to fire a stapling and cutting cartridge within cartridge assembly 308 of end effector 300.

The drive mechanism 160 includes a selector gearbox assembly 162 that is located immediately proximal relative to adapter assembly 200. Proximal to the selector gearbox assembly 162 is a function selection module 163 having a first (e.g., selector) motor 164 that functions to selectively move gear elements within the selector gearbox assembly 162 into engagement with an input drive component 165 having a second (e.g., drive) motor 166.

As illustrated in FIGS. 1-4, distal half-section 110a of upper housing portion 108 defines a connecting portion 108a configured to accept a corresponding shaft coupling assembly 214 of adapter assembly 200.

Figure 6:
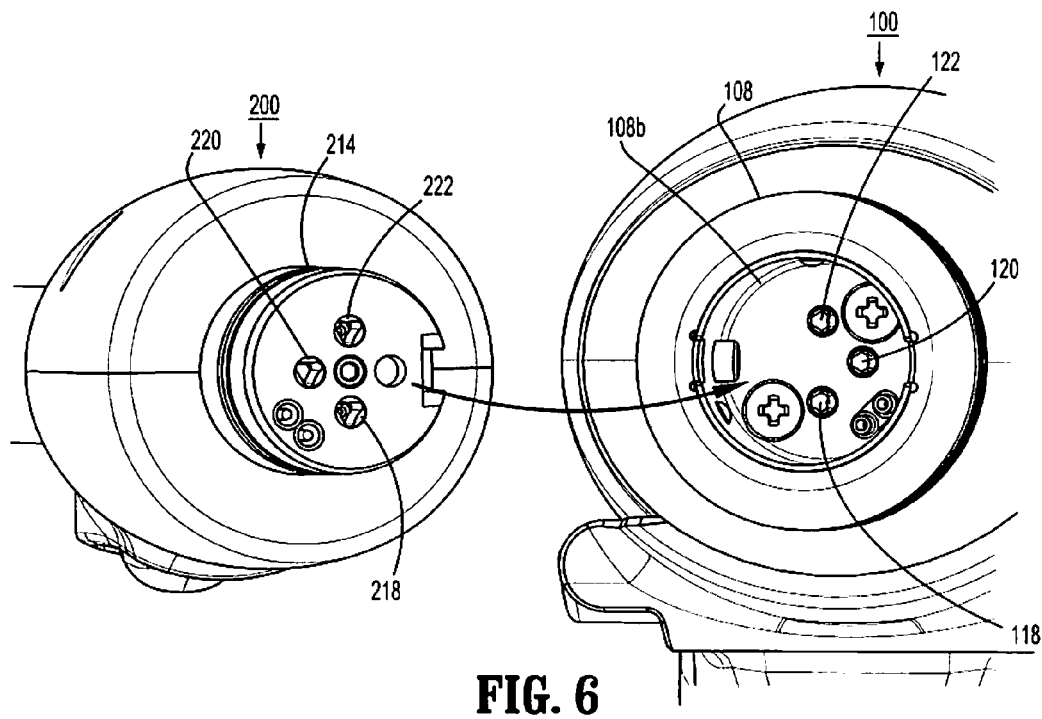
FIG. 6 is a front, perspective view of the surgical instrument of FIG. 1 with the elongated member separated therefrom, according to the present disclosure.
Figure 7:
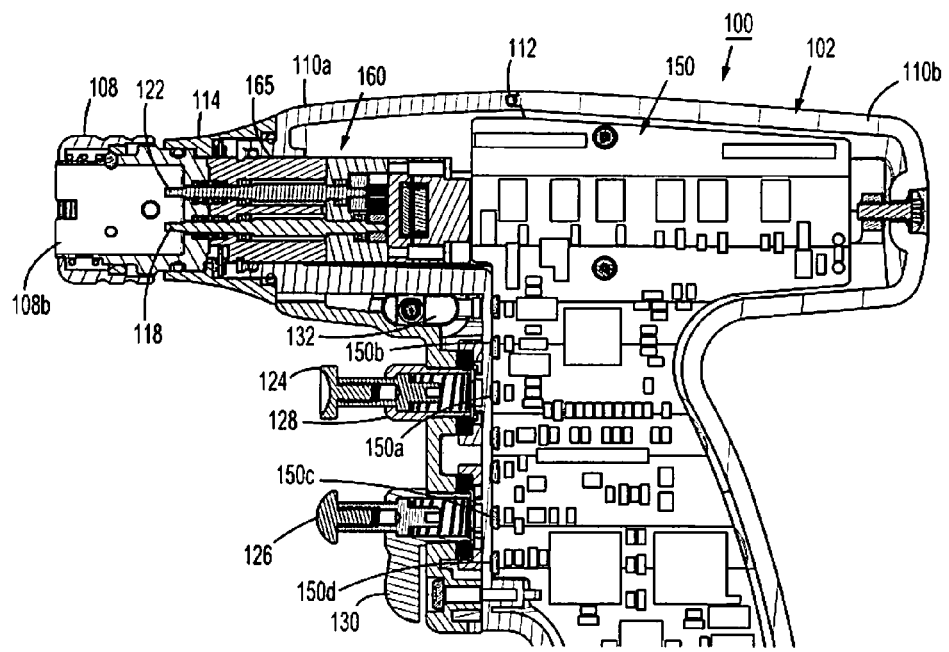
FIG. 7 is a cross-sectional side view of the surgical instrument of FIG. 1, as taken through 7-7 of FIG. 1, according to the present disclosure.
Figure 8:
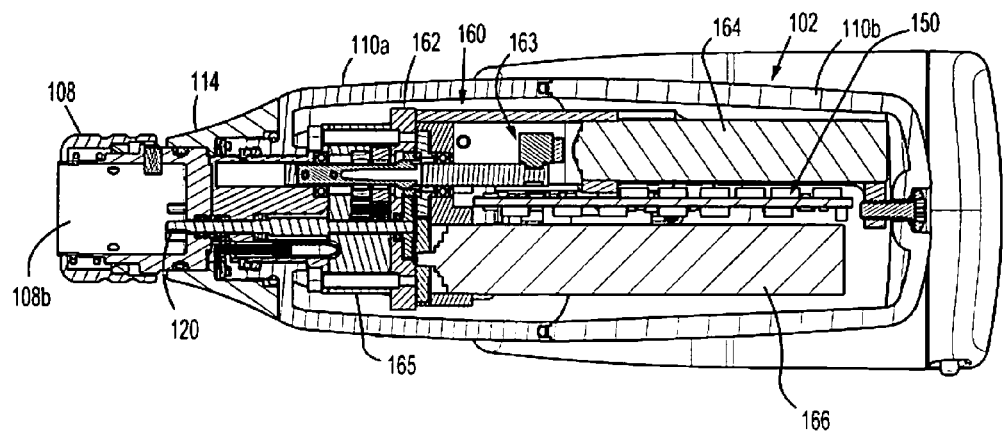
FIG. 8 is a top, cross-sectional view of the surgical instrument of FIG. 1, as taken through 8-8 of FIG. 1, according to the present disclosure.
Figure 9:
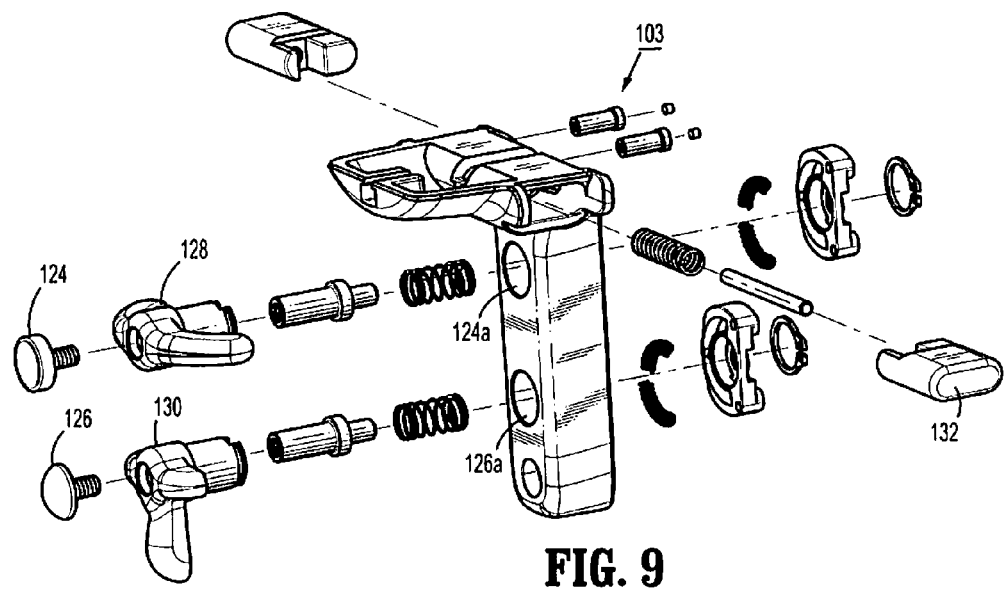
FIG. 9 is a perspective, disassembled view of a control assembly of the surgical instrument of FIG. 1, according to the present disclosure.

As illustrated in FIGS. 6-8, connecting portion 108a of surgical instrument 100 has a cylindrical recess 108b that receives the adapter assembly 200 when adapter assembly 200 is mated to surgical instrument 100. Connecting portion 108a houses three rotatable drive connectors 118, 120, 122.

With reference to FIG. 6, when adapter assembly 200 is mated to surgical instrument 100, each of rotatable drive connectors 118, 120, 122 of surgical instrument 100 couples with a corresponding rotatable connector sleeve 218, 220, 222 of adapter assembly 200. In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical instrument 100 causes a corresponding rotation of the corresponding connector sleeve 218, 220, 222 of adapter assembly 200.

In the above-described embodiments, the hand-held surgical instrument 100 may include a first (e.g., selector) motor 164 that functions to selectively move the selector gearbox assembly 162 gears into engagement with an input drive component having a second (e.g., drive) motor. In embodiments, other motor arrangements may be used, such as a different motor may be used for driving each of the connector sleeves. In further embodiments, other driving mechanisms for actuating the connector sleeves may be used, including, but not limited to, pneumatic and/or hydraulic drivers, solenoids, biasing members, and combinations thereof.

The mating of drive connectors 118, 120, 122 of surgical instrument 100 with connector sleeves 218, 220, 222 of adapter assembly 200 allows rotational forces to be independently transmitted via each of the three respective connector interfaces. The drive connectors 118, 120, 122 of surgical instrument 100 are configured to be independently rotated by drive mechanism 160. In this regard, the function selection module 163 of drive mechanism 160 selects which drive connector or connectors 118, 120, 122 of surgical instrument 100 is to be driven by the input drive component 165 of drive mechanism 160. The selector gearbox assembly 162 and the function selection module 163 are disclosed in more detail in a commonly-owned U.S. patent application Ser. No. 13/280,898, the entire contents of which is hereby incorporated by reference herein.

Since each of drive connectors 118, 120, 122 of surgical instrument 100 has a keyed and/or substantially non-rotatable interface with respective connector sleeves 218, 220, 222 of adapter assembly 200, when adapter assembly 200 is coupled to surgical instrument 100, rotational force(s) are selectively transferred from drive mechanism 160 of surgical instrument 100 to adapter assembly 200.

Figure 12:
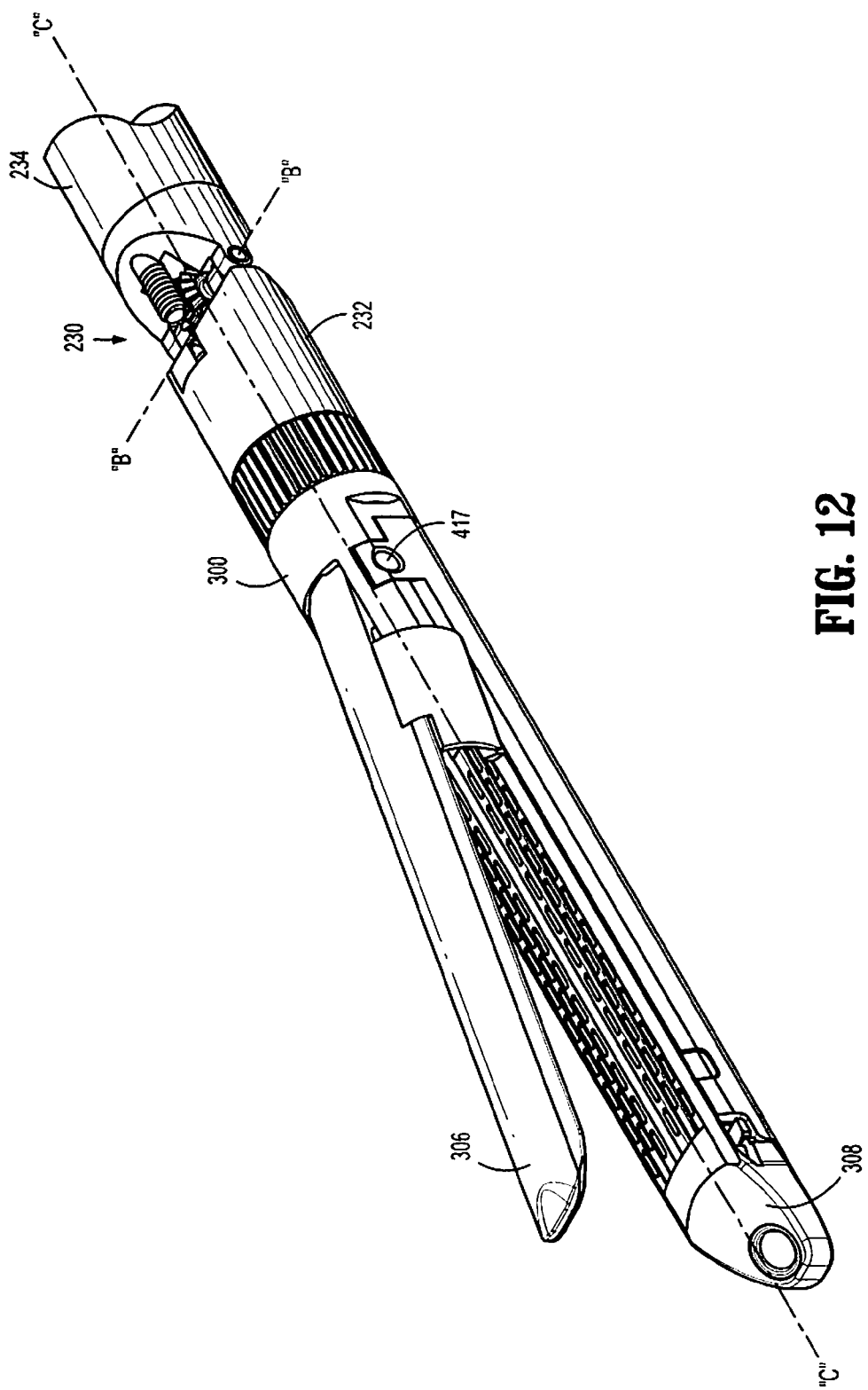
FIG. 12 is a perspective view of an end effector connected to a distal end of the adapter assembly of FIG. 1, oriented in a linear, non-articulated orientation, according to the present disclosure.

The selective rotation of drive connector(s) 118, 120 and/or 122 of surgical instrument 100 allows surgical instrument 100 to selectively actuate different functions of end effector 300. As discussed in greater detail below, selective and independent rotation of first drive connector 118 of surgical instrument 100 corresponds to the selective and independent opening and closing of tool assembly 304 of end effector 300, and driving of a stapling/cutting component of tool assembly 304 of end effector 300. Also, the selective and independent rotation of second drive connector 120 of surgical instrument 100 corresponds to the selective and independent articulation of tool assembly 304 of end effector 300 about an articulation axis "B-B" defined by a pin 505 (FIG. 12) that is transverse to longitudinal axis "A-A" (FIG. 2). In particular, the end effector 300 defines a second longitudinal axis "C-C" and is movable from a first position in which the second longitudinal axis "C-C" (FIG. 12) is substantially aligned with the first longitudinal axis "A-A" to at least a second position in which the second longitudinal axis "C-C" is disposed at a non-zero angle with respect to the first longitudinal axis "A-A." Additionally, the selective and independent rotation of third drive connector 122 of surgical instrument 100 corresponds to the selective and independent rotation of end effector 300 about longitudinal axis "A-A" relative to handle housing 102 of surgical instrument 100.

As illustrated in FIGS. 5 and 8, drive mechanism 160 includes a selector gearbox assembly 162; a function selection module 163, located proximal to the selector gearbox assembly 162, that functions to selectively move gear elements within the selector gearbox assembly 162 into engagement with second motor 166. Thus, drive mechanism 160 selectively drives one of drive connectors 118, 120, 122 of surgical instrument 100 at a given time.

As illustrated in FIGS. 1-3 and FIG. 9, handle housing 102 supports a control assembly 103 on a distal surface or side of intermediate housing portion 108. Control assembly 103, in cooperation with intermediate housing portion 108, supports a pair of finger-actuated control buttons 124, 126 and rocker devices 128, 130. In particular, control assembly 103 defines an upper aperture 124a for slidably receiving a first control button 124, and a lower aperture 126b for slidably receiving a second control button 126.

Each one of the control buttons 124, 126 and rocker devices 128, 130 includes a respective magnet (not shown) that is moved by the actuation of an operator. In addition, circuit board 150 includes, for each one of the control buttons 124, 126 and rocker devices 128, 130, respective Hall-effect switches 150a-150d that are actuated by the movement of the magnets in the control buttons 124, 126 and rocker devices 128, 130. In particular, located immediately proximal to the control button 124 is a first Hall-effect switch 150a (FIGS. 3 and 7) that is actuated upon the movement of a magnet within the control button 124 upon the operator actuating control button 124. The actuation of first Hall-effect switch 150a, corresponding to control button 124, causes circuit board 150 to provide appropriate signals to function selection module 163 and input drive component 165 of the drive mechanism 160 to close a tool assembly 304 of end effector 300 and/or to fire a stapling/cutting cartridge within tool assembly 304 of end effector 300.

Also, located immediately proximal to rocker device 128 is a second Hall-effect switch 150b (FIGS. 3 and 7) that is actuated upon the movement of a magnet (not shown) within rocker device 128 upon the operator actuating rocker device 128. The actuation of second Hall-effect switch 150b, corresponding to rocker device 128, causes circuit board 150 to provide appropriate signals to function selection module 163 and input drive component 165 of drive mechanism 160 to articulate tool assembly 304 relative to the adapter assembly 200. Advantageously, movement of rocker device 128 in a first direction causes tool assembly 304 to articulate relative to the adapter assembly 200 in a first direction, while movement of rocker device 128 in an opposite, e.g., second, direction causes tool assembly 304 to articulate relative to the adapter assembly 200 in an opposite, e.g., second, direction.

Furthermore, located immediately proximal to control button 126 is a third Hall-effect switch 150c (FIGS. 3 and 7) that is actuated upon the movement of a magnet (not shown) within control button 126 upon the operator actuating control button 126. The actuation of third Hall-effect switch 150c, corresponding to control button 126, causes circuit board 150 to provide appropriate signals to function selection module 163 and input drive component 165 of drive mechanism 160 to open tool assembly 304 of end effector 300.

In addition, located immediately proximal to rocker device 130 is a fourth Hall-effect switch 150d (FIGS. 3 and 7) that is actuated upon the movement of a magnet (not shown) within rocker device 130 upon the operator actuating rocker device 130. The actuation of fourth Hall-effect switch 150d, corresponding to rocker device 130, causes circuit board 150 to provide appropriate signals to function selection module 163 and input drive component 165 of drive mechanism 160 to rotate end effector 300 relative to handle housing 102 surgical instrument 100. Specifically, movement of rocker device 130 in a first direction causes end effector 300 to rotate relative to handle housing 102 in a first direction, while movement of rocker device 130 in an opposite, e.g., second, direction causes end effector 300 to rotate relative to handle housing 102 in an opposite, e.g., second, direction.

Figure 10:
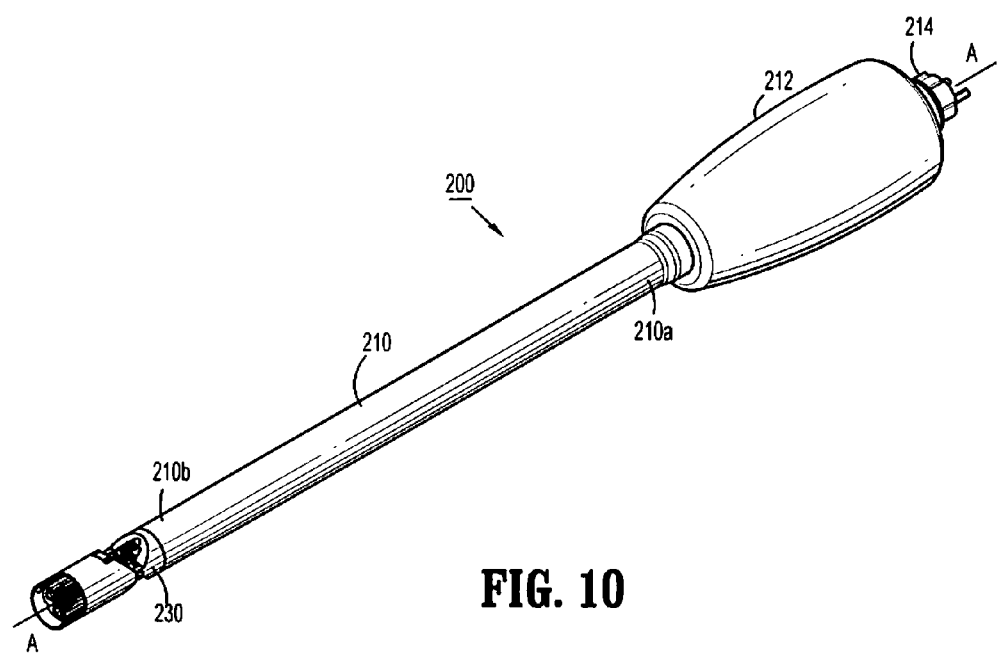
FIG. 10 is a perspective view of the adapter assembly of FIG. 1 having an articulating neck assembly, according to the present disclosure.

Turning now to FIGS. 1 and 10, adapter assembly 200 will be shown in detail and described. Adapter assembly 200 is configured to communicate the rotational forces of first, second and third rotatable drive connectors 118, 120, and 122 of surgical instrument 100 to end effector 300. As mentioned above, adapter assembly 200 is configured for selective connection to surgical instrument 100.

As seen in FIGS. 1, 6, 10, and 11 adapter assembly 200 includes an elongate, substantially rigid, elongate body portion 210 having a proximal end 210a and a distal end 210b; a transmission housing 212 connected to proximal end 210a of elongate body portion 210 and being configured for selective connection to surgical instrument 100. The adapter assembly 200 also includes an articulating assembly 230 disposed at the distal end 210b for coupling to the end effector 300.

In embodiments, the transmission housing 212 may include one or more gear train systems therein for varying a speed/force of rotation (e.g., increase or decrease) of first, second and/or third rotatable drive connectors 118, 120, and/or 122 of surgical instrument 100 before transmission of such rotational speed/force to end effector 300.

Transmission housing 212 of adapter assembly 200 is configured and adapted to connect to connecting portion 108a of upper housing portion 108 of surgical instrument 100. As seen in FIGS. 1 and 6, transmission housing 212 of adapter assembly 200 includes a shaft coupling assembly 214 supported at the proximal end 210a Adapter assembly 200 may include a first gear train system and a second gear train system, each disposed within transmission housing 212 and elongate body portion 210. Each gear train system is configured and adapted to vary a speed/force of rotation (e.g., increase or decrease) of first and second rotatable drive connectors 118 and 120 of surgical instrument 100 before transmission of such rotational speed/force to end effector 300. An adapter assembly having multiple gear trains is disclosed in more detail in a commonly-owned U.S. patent application Ser. No. 13/280,898, the entire contents of which is hereby incorporated by reference herein.

Figure 11:
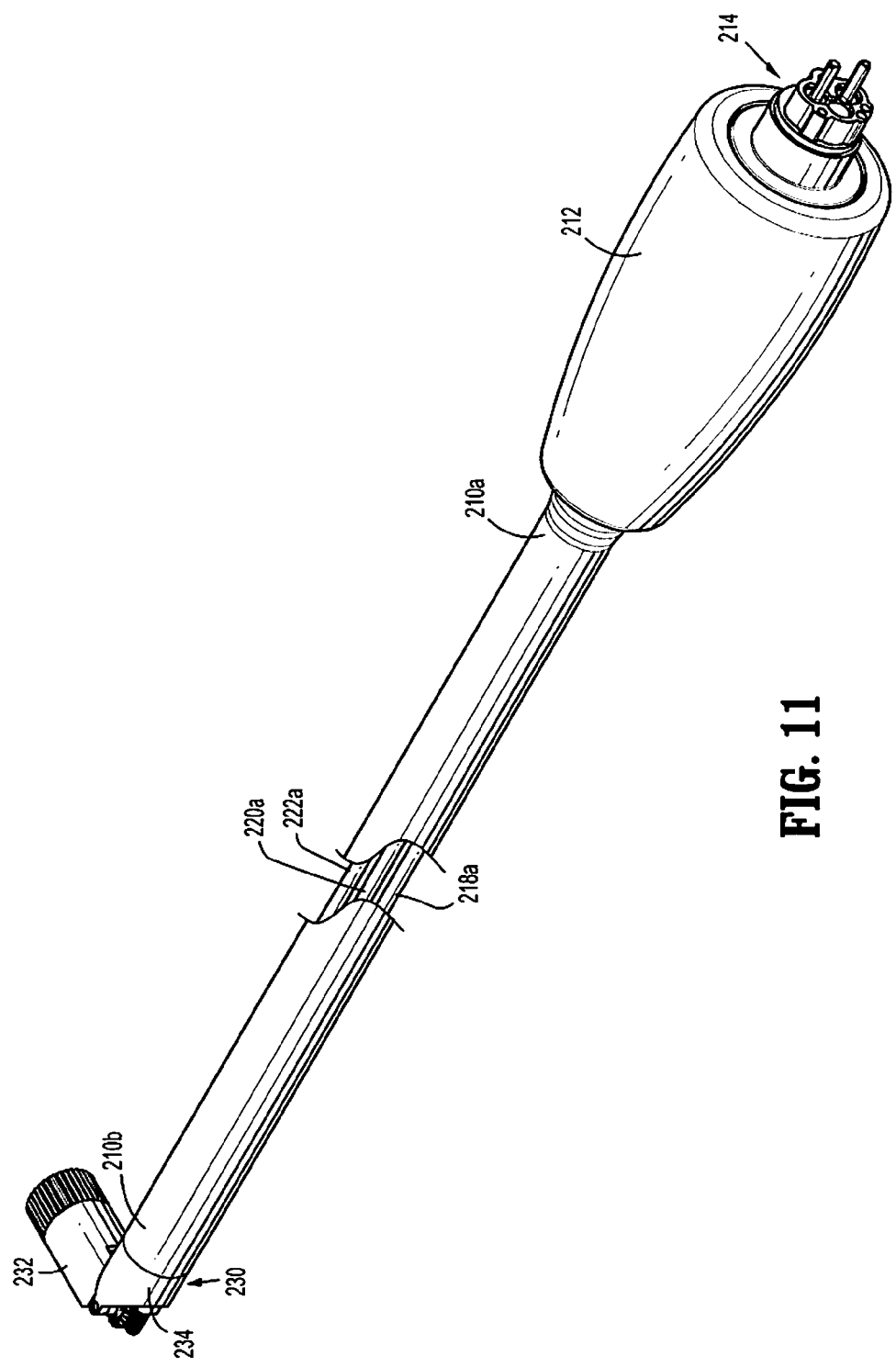
FIG. 11 is a perspective, partial cross-sectional view of the adapter assembly of FIG. 1, according to the present disclosure.

As seen in FIG. 11, adapter assembly 200 may rotatably support first, second, and third drive shafts 218a, 220a, 222a, which include a proximal end connected to transmission housing 212, namely, corresponding rotatable connector sleeve 218, 220, 222. Each of the drive shafts 218a, 220a, 222a also include a distal end extending to and operatively connected to the articulating assembly 230, as will be discussed in greater detail below. The elongate body portion 210 of adapter assembly 200 includes at least three longitudinally extending channels through body portion 210. The channels are configured and dimensioned to rotatably receive and support the drive shafts 218a, 220a, 222a, which may be connected to respective gear systems (not shown). Each of the drive shafts 218a, 220a, 222a are elongate and sufficiently rigid to transmit rotational forces from transmission housing 212 to articulating assembly 230, which are used to drive the end effector 300 as described in further detail below.

FIGS. 12-16 illustrate components and operation of the end effector 300. End effector 300 includes a pair of jaw members, which include a cartridge assembly 308 and an anvil 306. Cartridge assembly 308 houses one or more fasteners 433 (FIG. 13) that are disposed therewithin and is configured to deploy the fasteners 433 upon firing of instrument 100. The anvil 306 is movably (e.g., pivotally) mounted to the end effector 300 and is movable between an open position, spaced apart from cartridge assembly 308, and a closed position wherein anvil 306 is in close cooperative alignment with cartridge assembly 308, to thereby clamp tissue.

Figure 13:
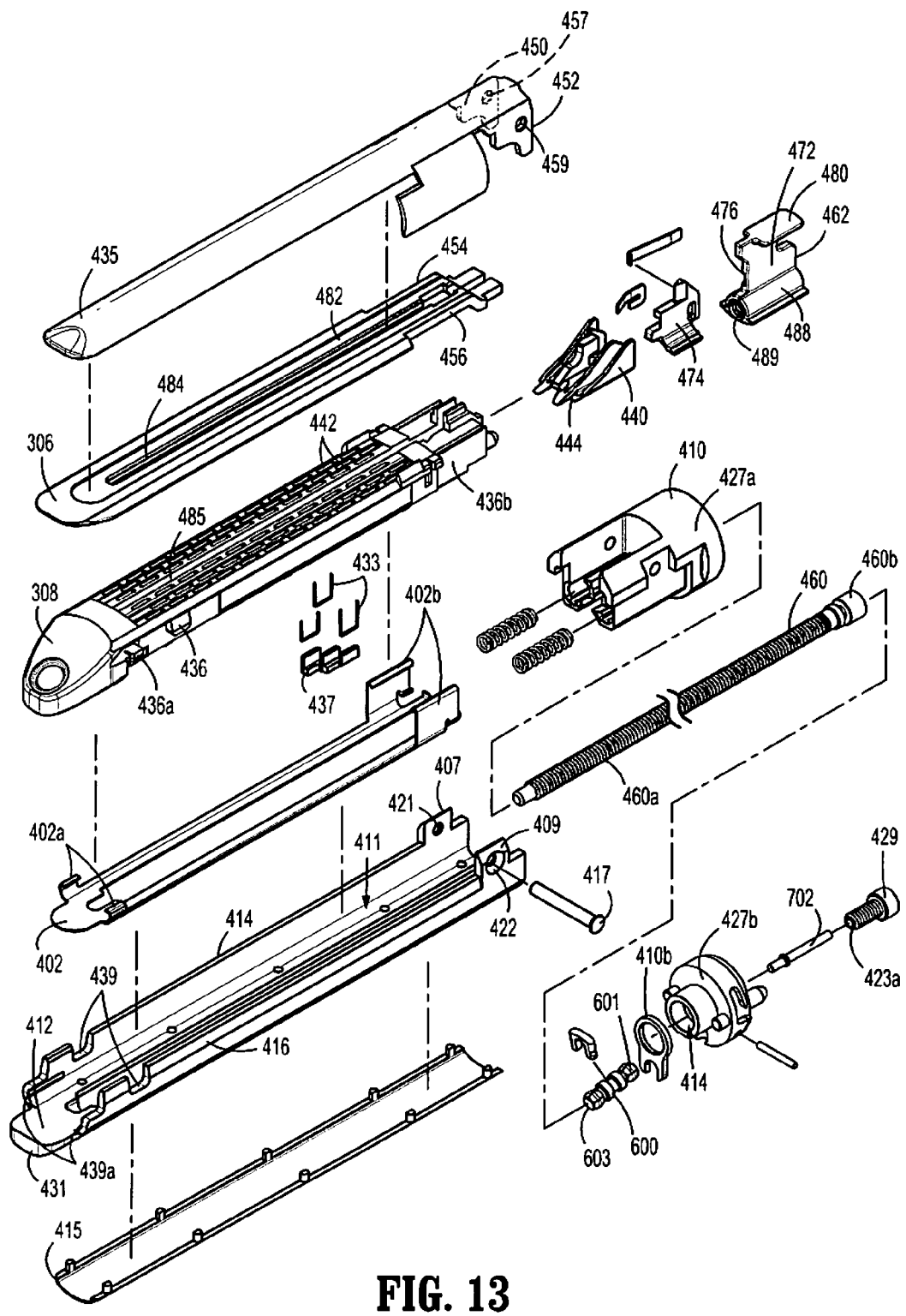
FIG. 13 is a disassembled view of the end effector of FIG. 12, according to the present disclosure.

Referring to FIG. 13, a disassembled view of the end effector 300 is shown. The end effector 300 also includes a carrier 431 having an elongate channel 411, a base 412 and two parallel upstanding walls 414 and 416 which include several mounting structures, such as notches 439, for supporting the cartridge assembly 308 and the anvil 306. A longitudinal slot 413 extends through the elongate channel 411.

The carrier 431 also includes a plate cover 415 disposed on a bottom surface thereof. The plate cover 415 is configured to frictionally engage with channel 411 of the carrier 431 and functions to protect tissue from moving parts along the exterior of carrier 431. The carrier 431 also includes a pair of tabs 407 and 409 disposed at a proximal end of respective walls 414, 416, and being configured for coupling to a housing portion 410 of end effector 300.

The carrier 431 also includes a holder plate 402 disposed on a top surface thereof. The holder plate 402 is configured to frictionally engage the carrier 431 and the cartridge assembly 308 to secure the fasteners 433 and pushers 437 therein. The holder plate 402 includes a pair of distal wings 402a and a pair of proximal wings 402b configured to engage distal tabs 436a and proximal tabs 436b of the cartridge assembly 308, respectively. The distal wings 402a of the holder plate 402 are also configured and dimensioned to engage slots 439a disposed at a distal end of the carrier 431 thereby securing the cartridge assembly 308 to the carrier 431.

With continuing reference to FIG. 13, the distal portion of channel 411 supports the cartridge assembly 308 which contains the plurality of surgical fasteners 433 and a plurality of corresponding ejectors or pushers 437. End effector 300 includes an actuation sled 440 having upstanding cam wedges 444 configured to exert a fastener driving force on the pushers 437, which drive the fasteners 433 from cartridge assembly 308, as described in more detail below. Cartridge assembly 308 is maintained within channel 411 by lateral struts 436 which frictionally engage corresponding notches 439 formed in the upper surfaces of channel walls 414 and 416. These structures serve to restrict lateral, longitudinal, and elevational movement of the cartridge assembly 308 within channel 411. In any of the embodiments disclosed herein, the cartridge assembly 308 can be removable and replaceable so that the end effector 300 can be reused within a particular surgery allowing for multiple firings of a single end effector 300.

A plurality of spaced apart longitudinal slots (not shown) extend through cartridge assembly 308 and accommodate the upstanding cam wedges 444 of actuation sled 440. The slots communicate with a plurality of pockets 442 within which the plurality of fasteners 433 and pushers 437 are respectively supported. The pushers 437 are secured by a pusher retainer (not shown) disposed below the cartridge assembly 308, which supports and aligns the pushers 437 prior to engagement thereof by the actuation sled 440. During operation, as actuation sled 440 translates through cartridge assembly 308, the angled leading edges of cam wedges 444 sequentially contact pushers 437 causing the pushers to translate vertically within slots 446, urging the fasteners 306 therefrom. The cartridge assembly 308 also includes a longitudinal slot 485 to allow for a knife blade 474 to travel therethrough, as described in more detail below.

Figure 14:
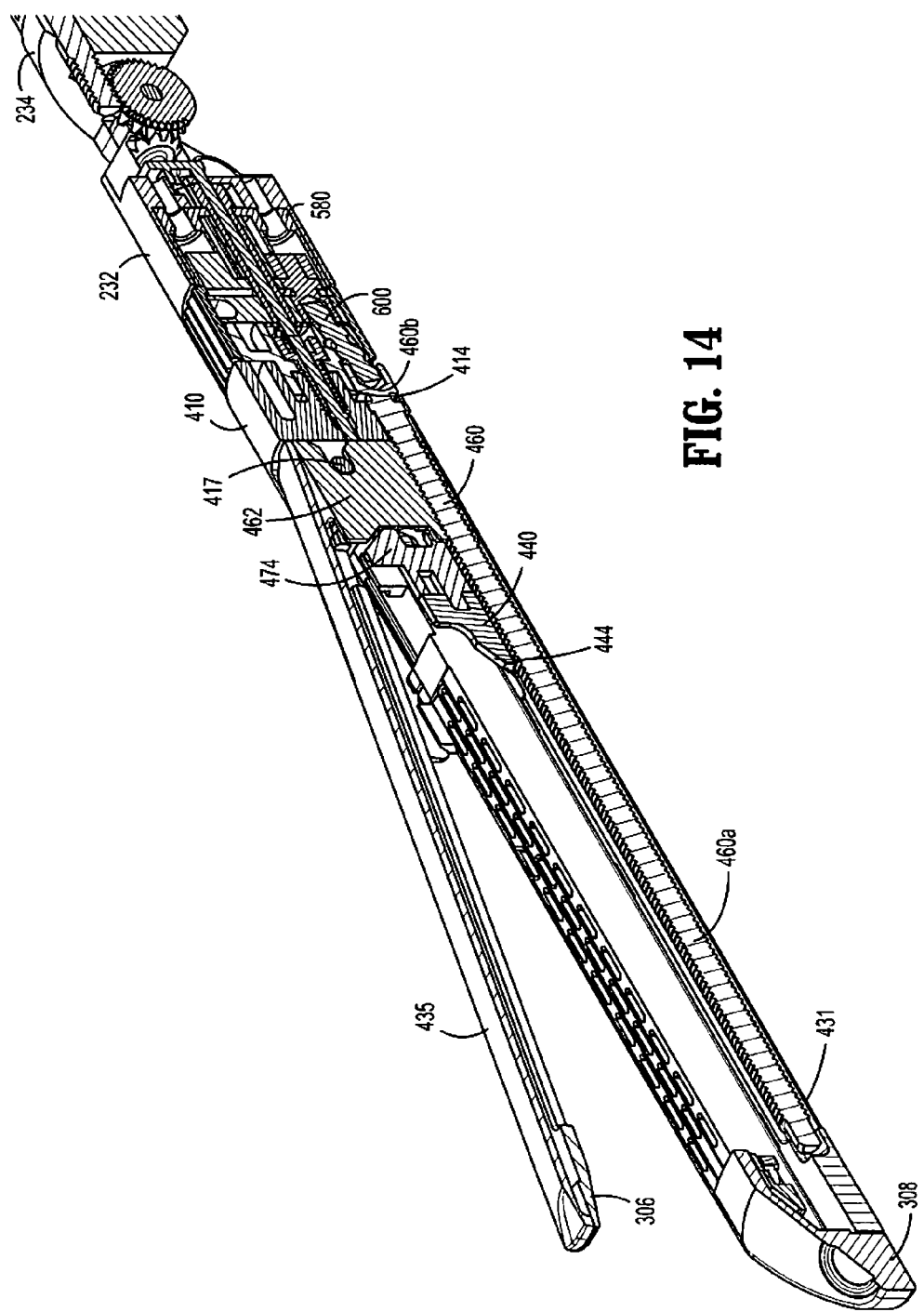
FIG. 14 is a perspective, cross-sectional view of the end effector of FIG. 12, according to the present disclosure.

With continuing reference to FIGS. 13 and 14, the end effector 300 includes an anvil cover 435 disposed over the anvil 306. The anvil cover 435 protects tissue from moving parts along the exterior of anvil 306. The anvil cover 435 includes opposed mounting wings 450 and 452 which are dimensioned and configured to engage detents 454 and 456 of the anvil 306, respectively. The mounting wings 450 and 452 function to align the anvil 306 with the cartridge assembly 308 during closure. The anvil 306 and the cover 435 are configured to remain in an open configuration until closed, as described in more detail below.

The anvil 306 is pivotally coupled to the carrier 431. The carrier 431 includes a pair of openings 421 and 422 formed in respective tabs 407, 409. The anvil cover 435 also includes a pair of opposed openings 457 and 459 found therein. A pivot pin 417, or a pair of pins, passes through the openings 421, 422, 457, and 459 allowing for pivotal coupling of the anvil 306 to the carrier 431 and the cartridge assembly 308.

As seen in FIGS. 13 and 14, end effector 300 further includes an axial drive screw 460 for transmitting the rotational drive forces exerted by the second drive shaft 220a, as described in further detail below, to actuation sled 440 during a stapling procedure. Drive screw 460 is rotatably supported in carrier 431 and includes a threaded portion 460a and a proximal engagement portion 460b. The drive screw 460 is rotatably secured by a thrust plate 410b within the distal housing member 410 such that the drive screw 460 may be rotated relative to the carrier 431. Distal housing member 410 of the end effector 300 is coupled to the proximal end of the carrier 431 via pivot pin 417. The housing member 410 includes a bore 414 (FIG. 14) defined therethrough that houses the engagement portion 460b therein. The distal tip of the drive screw 460 rests in a recess defined in the channel 411 of the carrier 431.

Figure 15:
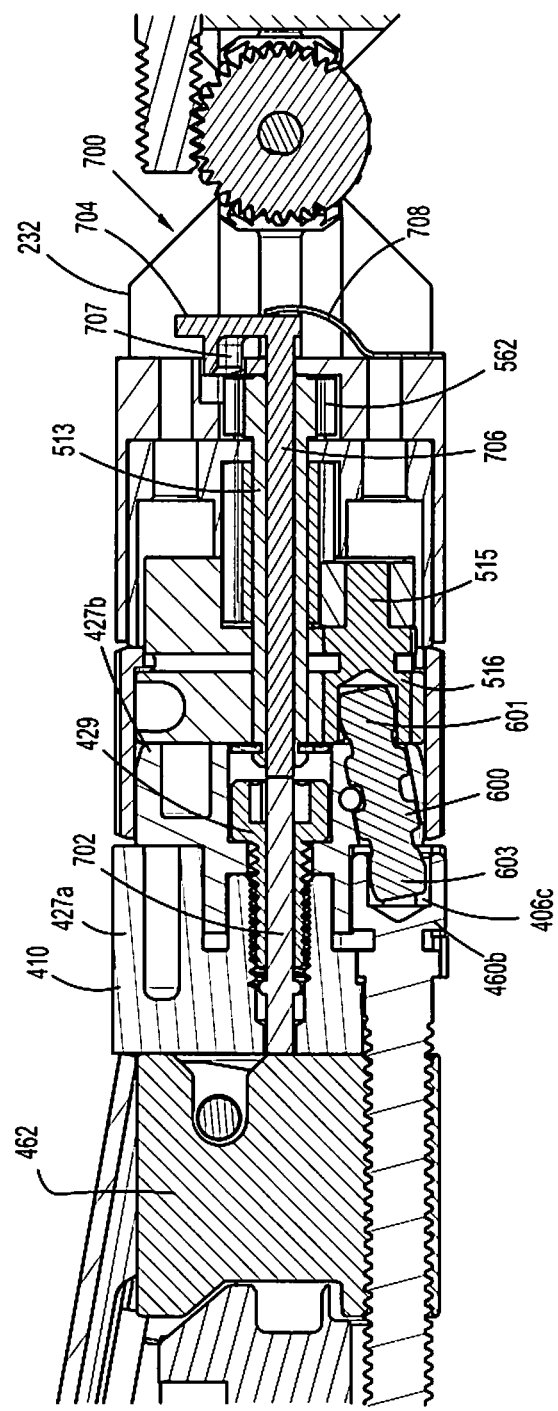
FIG. 15 is an enlarged, cross-sectional side view of the end effector of FIG. 12, according to the present disclosure.

As shown in FIGS. 13-15, the drive screw 460 is coupled to a drive linkage 600, which mechanically engages the second drive shaft 220a, as described in further detail below, and the drive screw 460 of end effector 300. The drive linkage 600, disposed within the housing portion 410, is off-axis with respect to the drive screw 460. In particular, the longitudinal axis defined by the drive linkage 600 is at a non-parallel (e.g., non-zero angle) angle with respect to a longitudinal axis defined by the drive screw 460. In embodiments, the drive linkage 600 may be disposed along the same longitudinal axis as the drive screw 460.

With reference to FIG. 15, the drive linkage 600 includes a proximal engagement portion 601 and a distal engagement portion 603. The proximal engagement portion 601 is configured to be engaged by a coupling member 515, and the distal engagement portion 603 is dimensioned and configured to engage the proximal engagement portion 460b of drive screw 460. In particular, the engagement portion 601 includes a faceted surface, which is configured and dimensioned to interface with a socket 516 of the coupling member 515, which has a corresponding faceted surface. The engagement portion 603 also includes a faceted surface, which is configured and dimensioned to interface with a socket 460c of the engagement portion 460b, which has a corresponding faceted surface. The mechanical coupling of the engagement portions 601 and 603 with the sockets 516 and 460c, respectively, occurs via abutment of the male faceted surfaces of the engagement portions 601 and 603 with corresponding female faceted socket 516 and 460c, which allows for transfer of rotational motion of the coupling member 515 to the drive linkage 600 and, in turn, to the drive screw 460. In embodiments, the drive linkage 600 may mechanically interface with the drive screw 460 and the coupling member 515 using any other suitable mechanical coupling, e.g., pinned.

With reference to FIGS. 13 and 14, end effector 300 further includes a drive beam 462 disposed within carrier 431. The drive beam 462 includes a vertical support strut 472 and an abutment surface 476, which engages the knife blade 474, which in turn, engages the actuation sled 440. The drive beam 462 also includes a cam member 480 disposed on top of the vertical support strut 472. Cam member 480 is dimensioned and configured to engage and translate with respect to an exterior camming surface 482 of anvil 306 to progressively clamp the anvil 306 against body tissue during firing.

A longitudinal slot 484 extends through the anvil 306 to accommodate the translation of the vertical strut 472. This allows the cam member 480 to travel in between the cover 435 and anvil 306 during firing. In embodiments, the anvil cover 435 may also include a corresponding longitudinal slot (not shown) formed on an underside thereof and is secured to an upper surface of anvil 306 to form a channel therebetween.

The drive beam 462 includes a retention portion 488 having a threaded bore 489 defined therethrough. The drive screw 460 is threadably coupled to the retention portion 480 through the bore 489, such that as the drive screw 460 is rotated, the drive beam 462 travels in a longitudinal direction along the longitudinal axis defined by the drive screw 460.

In use, as the drive screw 460 is rotated in a clock-wise direction, the drive beam 462 travels in a distal direction closing the anvil 306 as the cam member 480 pushes down on the camming surface 482 thereof. The drive beam 462 also pushes the sled 440 in the distal direction, which then engages the pushers 437 via the cam wedges 444 to eject the fasteners 433. The drive beam 462 may be made of any suitable first material including, but not limited to, plastics, metals, and combinations thereof. The first and second materials may be either same or different.

The knife blade 474 travels slightly behind actuation sled 440 during a stapling procedure to form an incision between the rows of fastener body tissue. As the drive beam 462 is driven in the distal direction, the abutment surface 476 of the vertical strut 472 pushes the knife blade 474, which then pushes sled 440 in the distal direction to eject the fasteners 433 and simultaneously dissect tissue with the knife blade 474. The knife blade 474 and the drive beam 462 travel through the longitudinal slots 484 and 485. The drive beam 462 closes the anvil as it is driven in the distal direction and also pushes the sled 440, which, in turn, ejects the fasteners 433 ahead of the knife blade 474. As the fasteners 433 are ejected they are deformed again the tissue-contacting (e.g., underside) surface of the anvil 306 having a plurality of anvil pockets (not shown).

With reference to FIGS. 11, 12, and 14-17A, the articulating assembly 230 is shown. The assembly 230 includes a distal joint member 232 for coupling to a proximal end of the end effector 300 and a proximal joint member 234 coupled to the distal end 210b of the body portion 210.

With reference to FIGS. 13 and 16-21 the housing portion 410 of the end effector 300 includes one or more posts 410a for insertion into one or more corresponding bores 580a within a socket 580. The socket 580 is rotationally disposed within the joint member 232. In particular, the socket 580 is disposed within a spacer 232a and includes a textured ring 232b disposed on an outer surface thereof. This allows the socket 580 to be rotated about the longitudinal axis "C-C" (FIG. 12) by a shaft 513 that is longitudinally arranged within the joint member 232, as described in further detail below.

Figure 16:
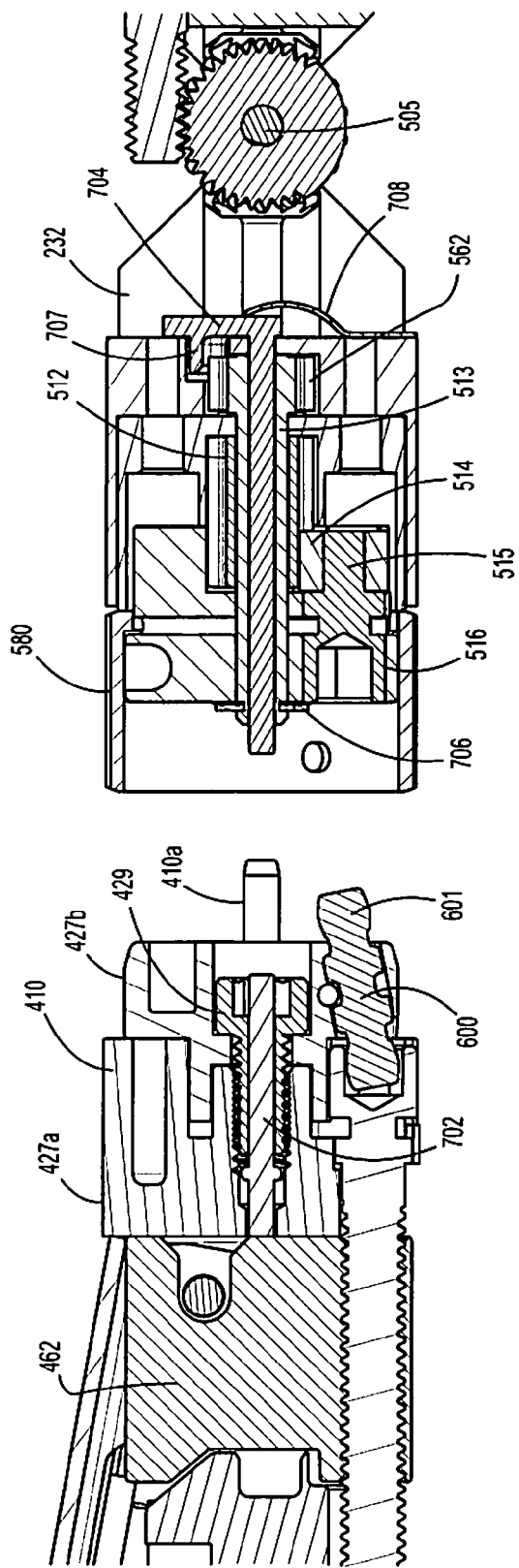
FIG. 16 is an enlarged, cross-sectional side view of the end effector of FIG. 12 disconnected from the articulating neck assembly, according to the present disclosure.

The shaft 513 includes one or more facets 513a such that the shaft 513 is keyed to a central bore 580b of the socket 580. This allows for rotation of the socket 580 along with the shaft 513. As shown in FIG. 16, during insertion the proximal engagement portion 601 of the drive linkage 600 also engages the socket 516 of the coupling member 515, which actuates the drive screw 460 as described in further detail below.

Figures 17A, 17B:
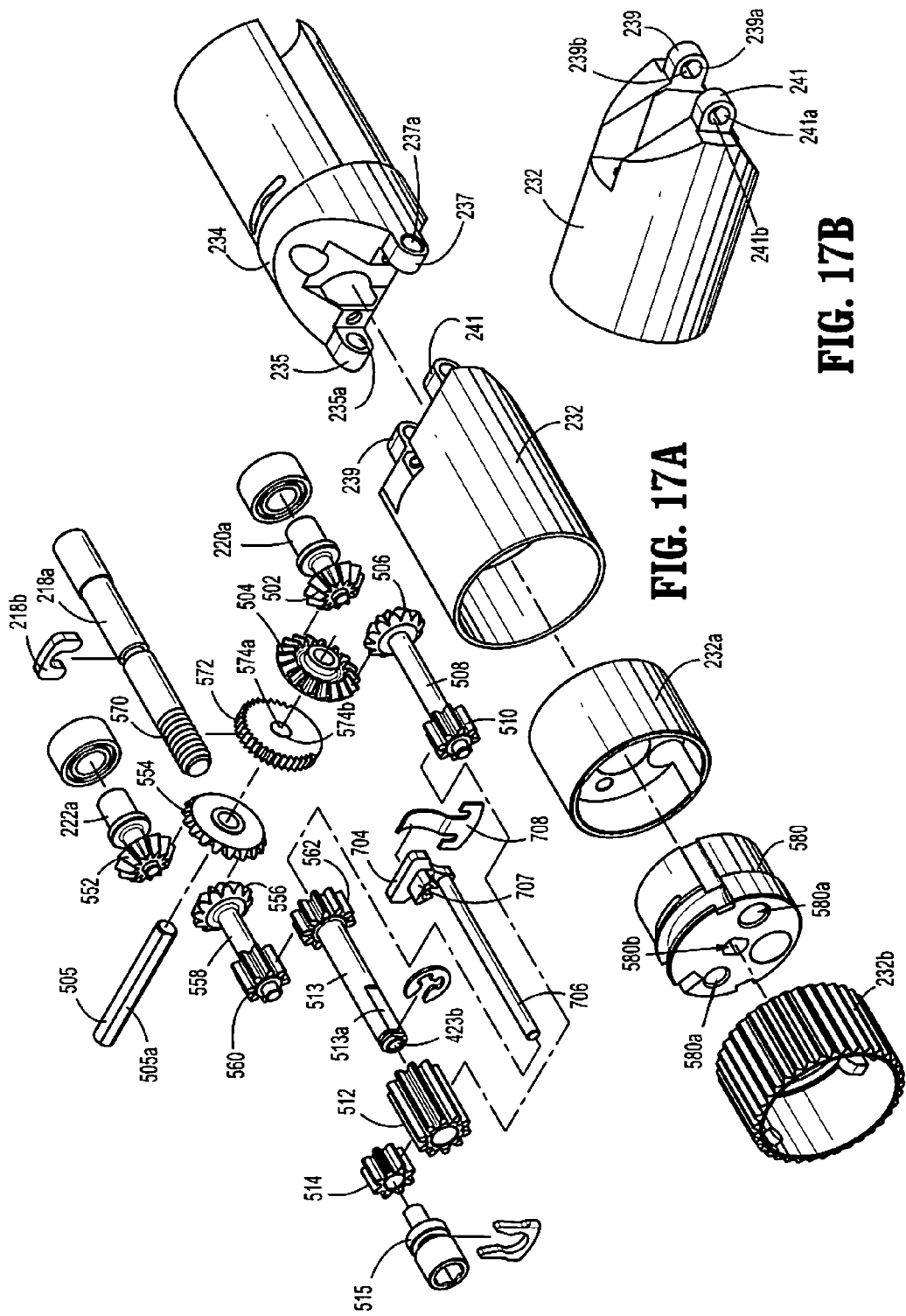
FIG. 17A is a disassembled view of the articulating neck assembly according to the present disclosure.
FIG. 17B is a perspective view of part of the articulating neck assembly according to the present disclosure.
Figure 22:
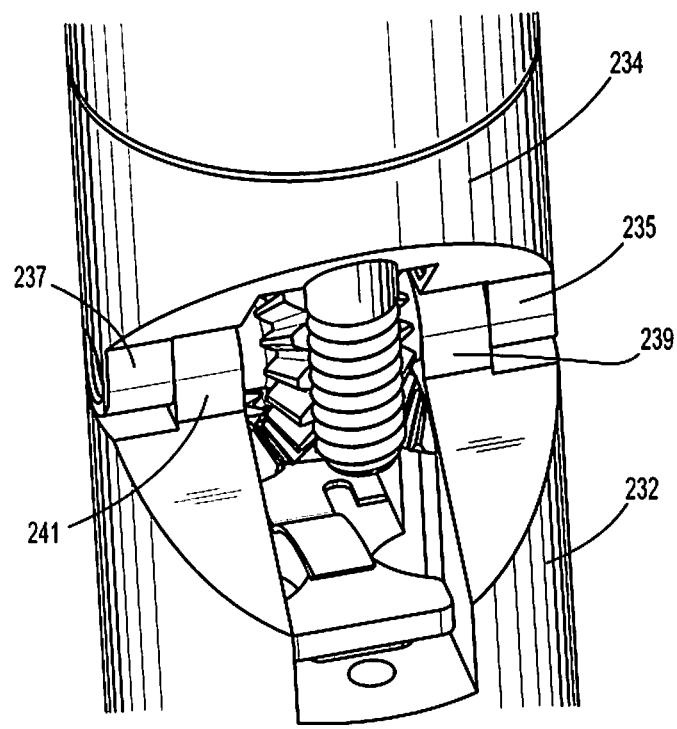
FIG. 22 is a top perspective view of the articulating neck assembly according to the present disclosure.

With reference to FIGS. 17A-19, the proximal joint member 234 and the distal joint member 232 are configured and dimensioned as a clevis to interface with a pin 505. The pin 505 includes one or more longitudinal facets 505a along at least a portion of the pin 505. The proximal joint member 234 of the neck assembly 230 includes a pair of opposing arms 235, 237 including a pair of opposing circular bores 235a, 237a, respectively, allowing the pin 505 to be rotationally coupled within the bores 235a, 237a of opposing arms 235, 237. With reference to FIGS. 17A-B, the joint member 232 of the assembly 230 also includes a pair of opposing arms 239, 241 including a pair of opposing bores 239a, 241a. With reference to FIG. 17B, each of the bores 239a, 241a includes a facet 239b, 241b, such that when the pin 505 is inserted into the bores 235a, 237a, 239b, 241b, the pin 505 can rotate freely within the bores 235a, 237a. This secures the joint member 232 to the pin 505 about the bores 239a, 241a via mating of the facet 505a of the pin 505 with the facets 239b, and 24 lb. Since the pin 505 is keyed to the bores 239a, 241a of the joint member 232 and is free-floating within the bores 235a, 237a of the proximal joint member 234, the joint member 232 along with the end effector 300 may be freely rotated with respect to the proximal joint member 234 about a articulation axis "B-B" (FIG. 12) defined by the pin 505 as shown in FIG. 22 and described in further detail below.

Figure 18:
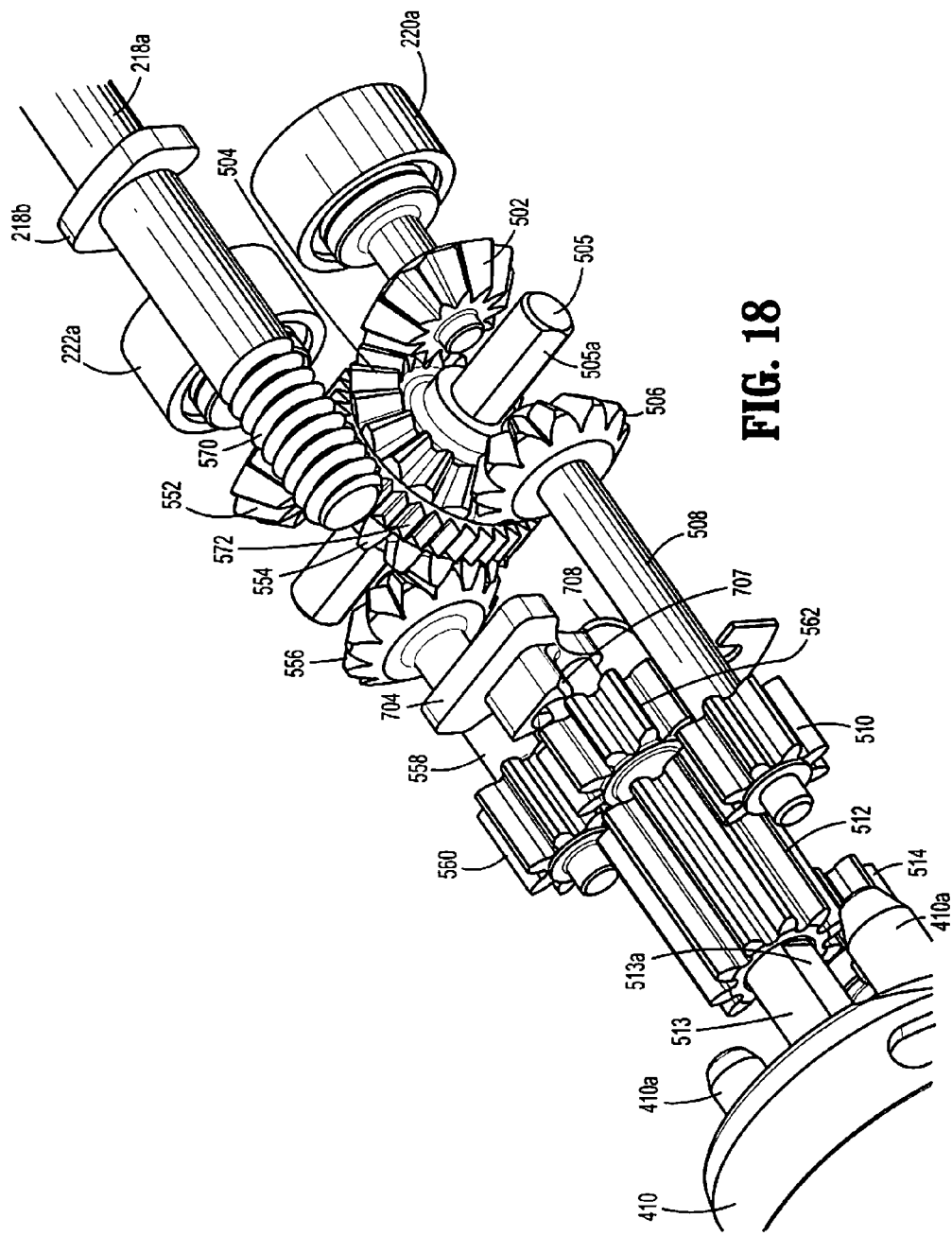
FIG. 18 is a top perspective, partially-disassembled view of the articulating neck assembly according to the present disclosure.
Figure 19:
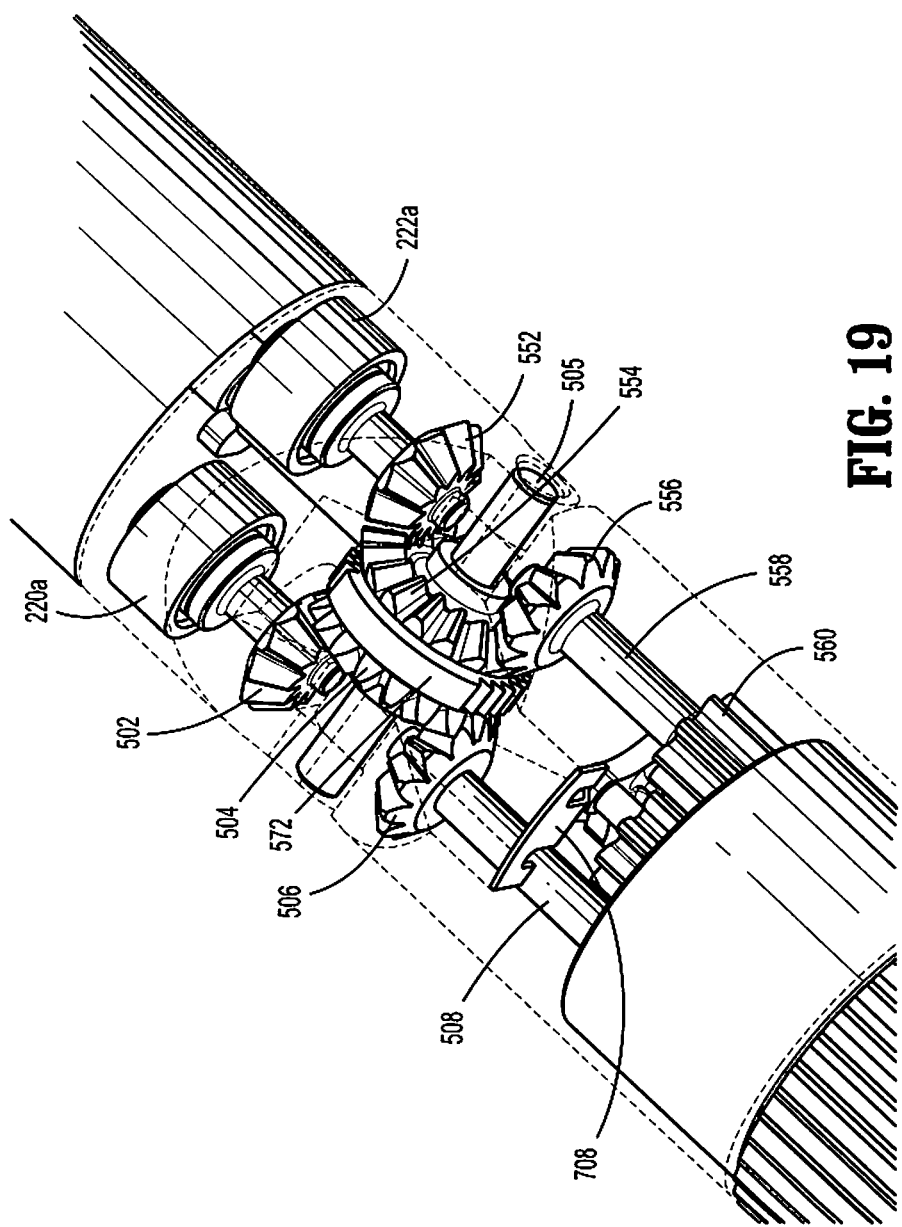
FIG. 19 is a bottom perspective, partially-disassembled view of the articulating neck assembly according to the present disclosure.
Figure 20:
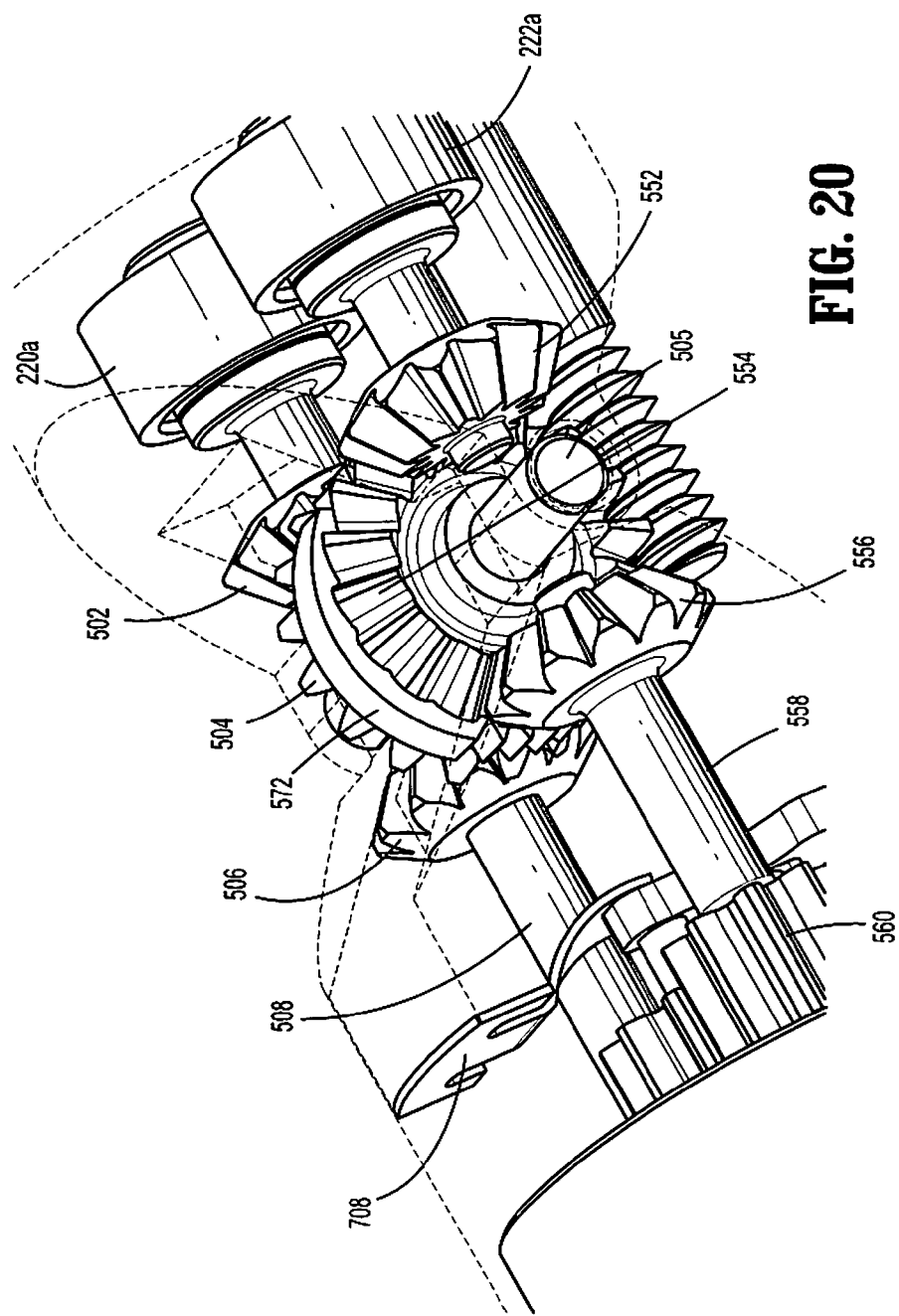
FIG. 20 is a side perspective, partially-disassembled view of the articulating neck assembly according to the present disclosure.
Figure 21:
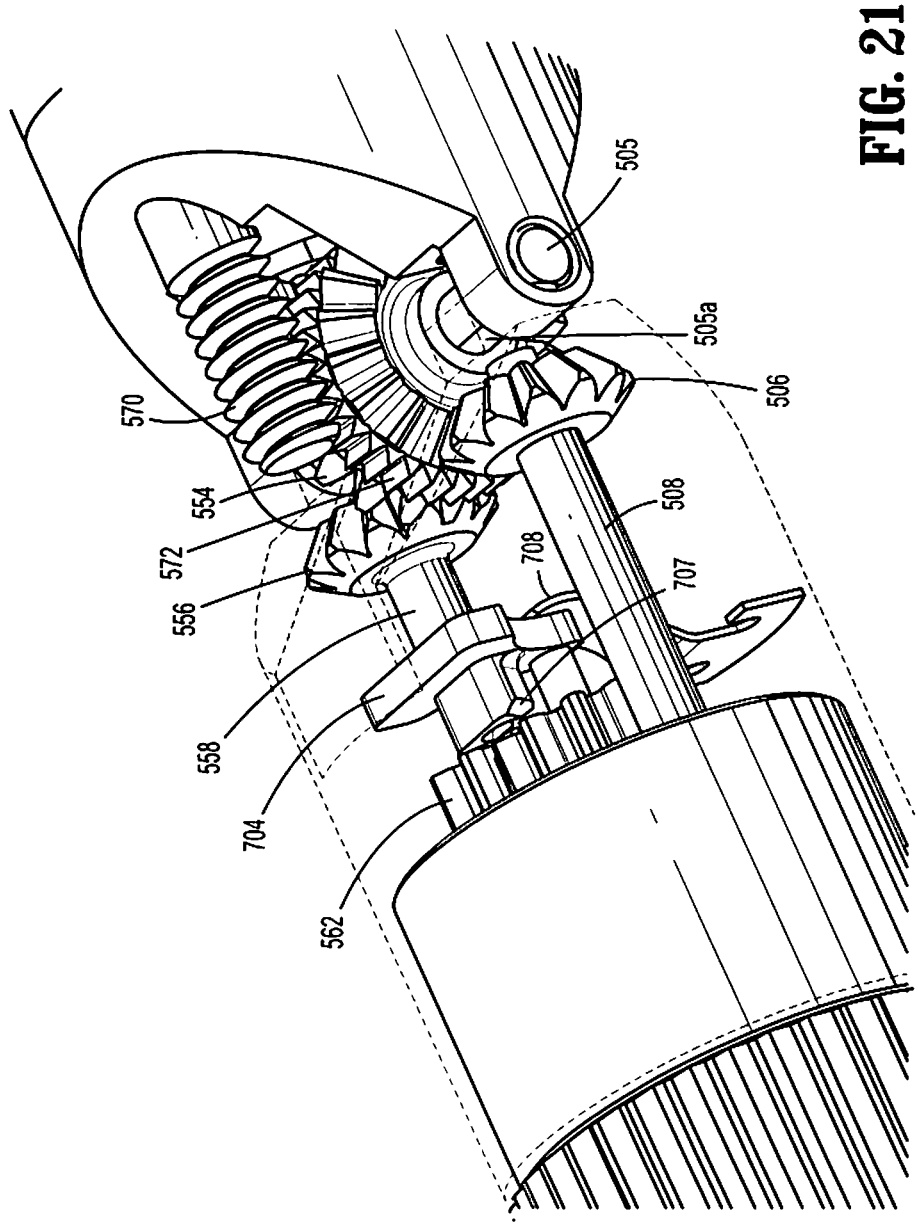
FIG. 21 is a top perspective, partially-disassembled view of the articulating neck assembly according to the present disclosure.

With reference to FIGS. 17A and 18, the assembly 230 also includes the second (e.g., actuating/firing) drive shaft 220a, which may be axially rotatable within the body portion 210. The drive shaft 220a includes a second gear element 502 coupled thereto and configured to rotate therewith about a longitudinal axis defined by the drive shaft 220a. The gear element 502 is meshingly engaged with a first transfer gear element 504. The gear element 504 is held in position by the pin 505 and is configured to rotate about the pin 505.

The gear element 504 is also meshingly engaged with a gear element 506 within the joint member 232. The gear elements 502, 504, 506 are bevel gears allowing for meshing engagement thereof even as the joint member 232 and the end effector 300 are pivoted with respect to the body portion 210. The gear element 502 rotates about a longitudinal axis parallel with the axis "A-A." The gear element 504 rotates about the axis "B-B" (FIG. 12) and the gear element 506 rotates about a longitudinal axis parallel with the axis "C-C" (FIGS. 2 and 10). The gear element 506 is connected to a gear element 510 by a shaft 508. The gear element 506, the gear element 510, and the shaft 508 rotate within the joint member 232 about a longitudinal axis defined by the central axis of the shaft 508. The gear element 510 is, in turn, meshingly engaged with a gear element 512 that rotates about the shaft 513 that is longitudinally arranged within the joint member 232. The gear element 512 is meshingly engaged with a gear element 514 of the coupling member 515. The coupling member 515 includes a shaft portion that extends distally to the socket 516, which is coupled to drive linkage 600 as described above. Rotation of the drive shaft 220a results in rotation of the gear elements 502, 504, 506, 510, 512, 514 and the socket 516, which in turn, rotates the drive screw 460 via the drive linkage 600 thereby actuating the firing process as described above.

With continued reference to FIGS. 16-21, the assembly 230 also includes the third (e.g., rotating) drive shaft 222a, which may be axially rotatable within the body portion 210. The drive shaft 222a includes a third gear element 552 coupled thereto and configured to rotate therewith about a longitudinal axis defined by the drive shaft 222a. The gear element 552 is meshingly engaged with a second transfer gear element 554. The gear element 554 is held in position by the pin 505 and is configured to rotate about the pin 505.

Figure 23:
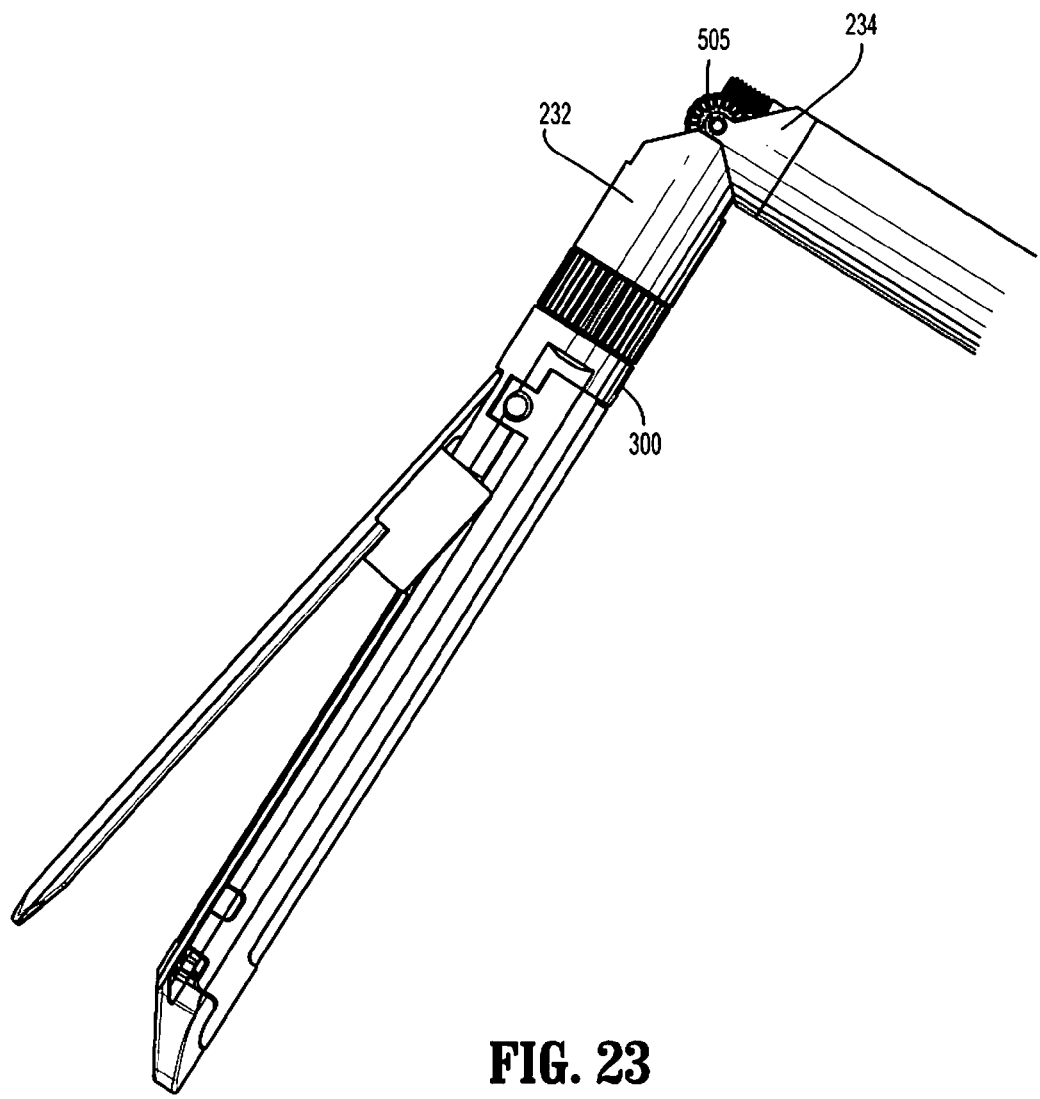
FIG. 23 is a side view of the articulating neck assembly in an articulated orientation, according to the present disclosure.

The gear element 554 is also meshingly engaged with a gear element 556 within the joint member 232. The gear elements 552, 554, 556 are bevel gears allowing for meshing engagement thereof even as the joint member 232 and the end effector 300 are pivoted with respect to the body portion 210. The gear element 552 rotates about a longitudinal axis parallel with the axis "A-A." The gear element 554 rotates about the axis "B-B" and the gear element 556 rotates about a longitudinal axis parallel with the axis "C-C." Use of the bevel gears, namely, the gear elements 502, 504, 506, 552, 554, 556, allows for tightest possible 90° bend angle of the joint member 232 during articulation with respect to the body portion 210 of the adapter assembly 200 as shown in FIG. 23, which shows the joint member 232 pivoted with respect to the joint member 234.

With continued reference to FIGS. 16-21, the gear element 556 is connected to a gear element 560 by a shaft 558. The gear element 556, the gear element 560, and the shaft 558 rotate within the joint member 232 about a longitudinal axis defined by the central axis of the shaft 558. The gear element 560 is, in turn, meshingly engaged with a gear element 562, which is fixedly coupled to the shaft 513, such that rotation of the gear element 562 results in rotation of the shaft 513. As described above, the socket 580 is securely coupled to the shaft 513, such that as the shaft 513 is rotated in either clockwise or counterclockwise direction about the longitudinal axis "C-C" the socket 580 is also rotated in the same direction. Since the end effector 300 is engaged with the socket 580 as described above, the end effector 300 is similarly rotated by the shaft 513. The end effector 300 is configured to rotate about its own longitudinal axis in this manner.

The present disclosure also provides for a rotation lockout assembly 700 for preventing rotation of the end effector 300 during firing. This allows for prevention of tissue damage due to the torque generated during the firing process which would otherwise backfeed the gears within the neck assembly 230 and inadvertently rotate the end effector.

With reference to FIGS. 13, 15, and 17A, the housing 410 may include a distal portion 427a and a proximal portion 427b interconnected by a bolt 429 with the bore 423a (FIG. 13) defined therethrough. The shaft 513 disposed within the joint member 232 includes a bore 423b (FIG. 17A) defined therethrough. The bores 423a and 423b are in longitudinal alignment.

With reference to FIGS. 15-17A, the lockout assembly 700 includes a push rod 702 disposed within the bore 423a and a locking member 704 disposed within the joint member 232. The locking member 704 includes a rod 706 disposed within the bore 423b. The distal end of the rod 706 is in contact with a proximal end of the push rod 702, such that longitudinal movement of either the push rod 702 or the locking member 704 is translated therebetween. The locking member 704 also includes one or more lock lugs 707 configured and dimensioned to meshingly engage the gear element 562. The locking mechanism 700 also includes a spring 708, which is coupled to the joint member 232 and pushes the locking member 704 in a distal direction.

With reference to FIG. 16, prior to insertion of the end effector 300 into the joint member 232, the locking member 704 is engaged with the lock lug 707 thereof preventing actuation of the coupling member 515. As shown in FIGS. 15 and 18, after insertion of the end effector 300, the drive beam 462 is in its proximal most position since it has not been fired and therefore abuts the distal end of the push rod 702. This moves the push rod 702 proximally, which also moves the locking member 704 in a proximal direction to disengage the lock lug 707 from the teeth of the gear element 562. The disengagement of the locking member 704 allows for rotation of the shaft 513, the socket 580, and in turn, the end effector 300 in either clockwise or counterclockwise direction about the longitudinal axis "C-C."

Figure 24:
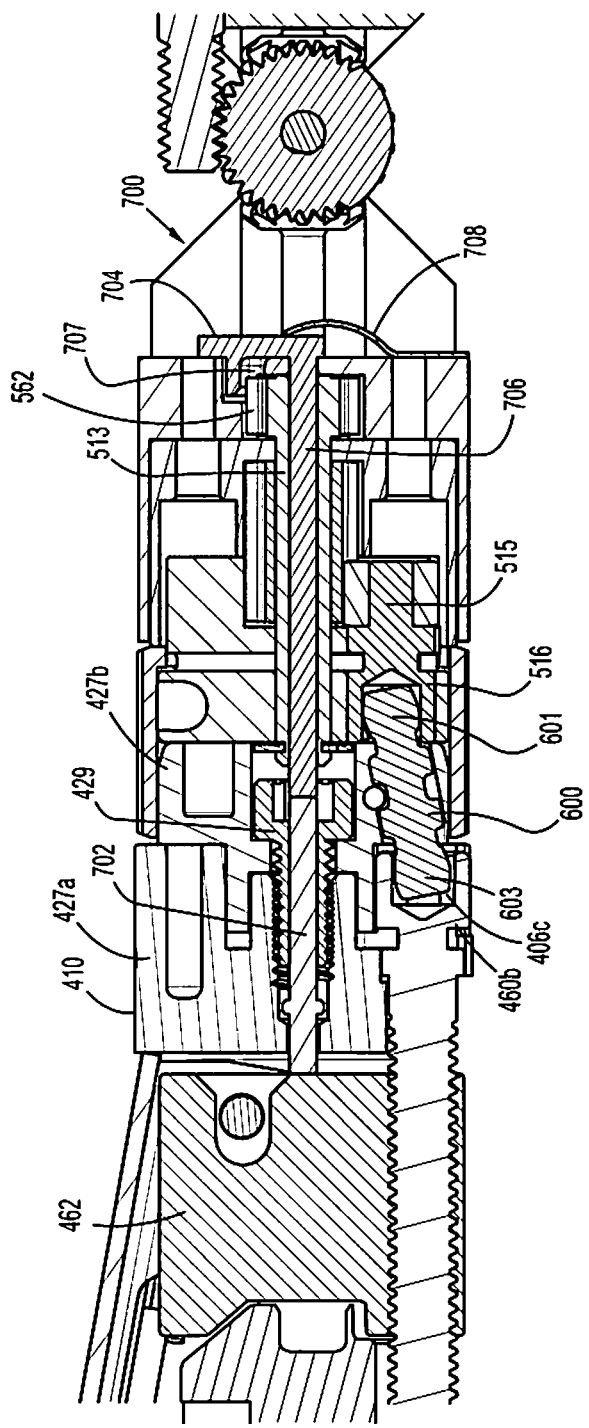
FIG. 24 is an enlarged, cross-sectional side view of the end effector of FIG. 12 connected to the articulating neck assembly, according to the present disclosure.

Once the desired rotational position is achieved firing may be commenced as described above. Firing moves the drive beam 462 distally, which allows the push rod 702 along with the locking member 704 to travel distally due to the biasing forces of the spring 708 as shown in FIG. 24. This moves the lock lug 707 of the locking member 704 into engagement with the gear element 562 preventing rotation of the end effector 300 during the firing process.

With reference to FIGS. 17A, 18 and 25-27, the assembly also includes the first (e.g., pivoting) drive shaft 218a, which may be axially rotatable within the body portion 210. The drive shaft 218a includes a first gear element 570 at its distal end, which is configured as a worm gear. The gear element 570 is meshingly engaged with a pivoting gear element 572, which is configured as a worm wheel drive. The gear element 572 includes a bore 574a therethrough having a facet 574b. The gear element 572 is disposed between the gear elements 504, 554 and is secured to the pin 505 about the bore 574a via mating of the facet 505a of the pin 505 with the facet 574b of bore 574a of gear element 572 in a keyed relationship. Thus, the gear element 572 is secured to the pin 505 along with the joint member 232, which allows for rotation of the joint member 232 along with the end effector 300 with respect to the body portion 210 about the articulation axis "B-B" defined by the pin 505 as described in further detail below.

Figure 25:
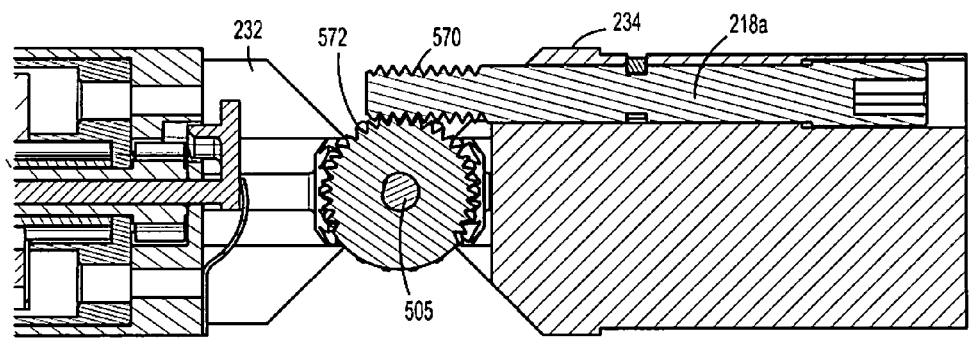
FIG. 25 is a cross-sectional side view of the end effector of FIG. 12 connected to the articulating neck assembly oriented in a linear, non-articulated orientation, according to the present disclosure.
Figure 26:
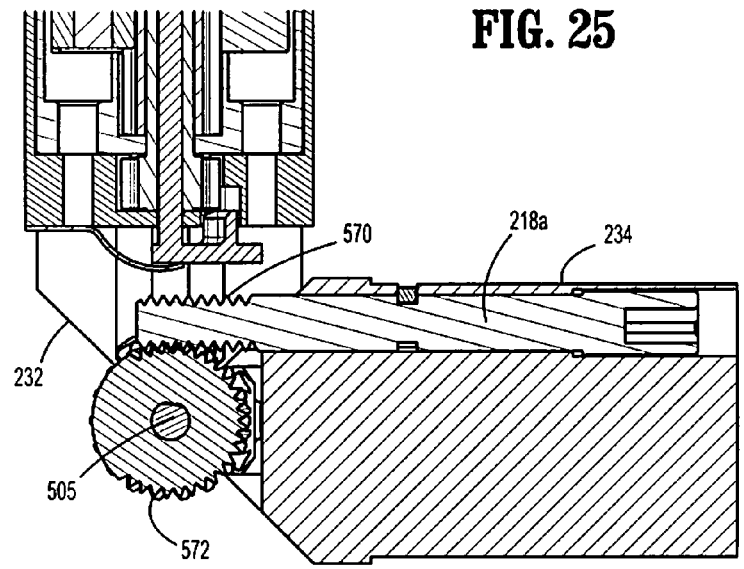
FIG. 26 is a cross-sectional side view of the end effector of FIG. 12 connected to the articulating neck assembly oriented in a first articulated orientation, according to the present disclosure.
Figure 27:
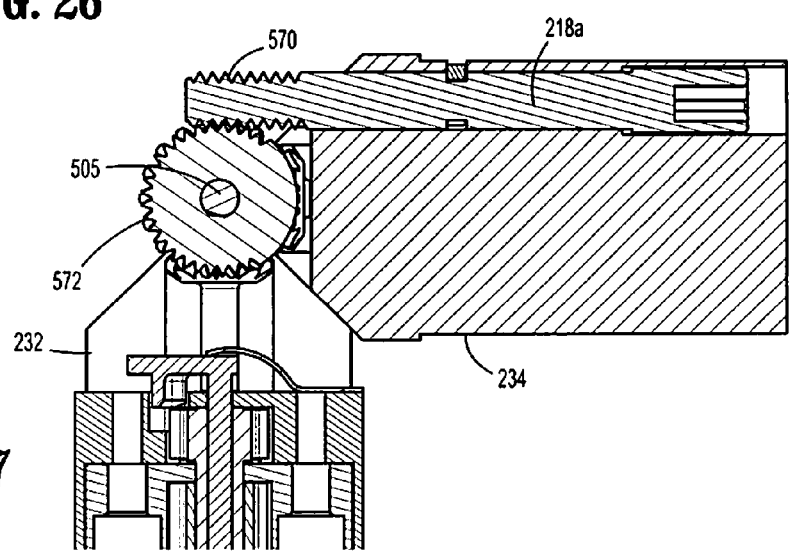
FIG. 27 is a cross-sectional side view of the end effector of FIG. 12 connected to the articulating neck assembly oriented in a second articulated orientation, according to the present disclosure.

As shown in FIGS. 25-27, articulation of the joint member 232 about the articulation axis "B-B" is imparted by rotation of the drive shaft 218a about its longitudinal axis and simultaneous longitudinal movement of the drive shaft 218a along its longitudinal axis, which in turn, rotates the gear element 572 via the gear element 570. Simultaneous rotational and longitudinal movement of the drive shaft 218a may be accomplished via a complementary worm gear mechanism at its proximal end. Since the gear element 572 is securely coupled to the pin 505, rotation of the gear element 572 rotates the pin 505 and the joint member 232, which is also securely coupled thereto as described above. The drive shaft 218a includes a thrust plate 218b that acts as a stop member preventing longitudinal movement of the drive shaft 218a beyond a certain point, which in turn, prevents rotation of the joint member 232 and the end effector 300 beyond a desired stopping point. In embodiments, the joint member 232 may be rotated about the articulation axis "B-B" up to about 300°, with about 150° in either direction from the first aligned position in which the second longitudinal axis "C-C" is substantially aligned with the first longitudinal axis "A-A." In further embodiments, the joint member 232 may be rotated about the articulation axis "B-B" up to about 180°, with about 90° in either direction from the first aligned position.

The gearing relationship between the gear elements 570 and 572 allows for precise pivoting of the end effector 300 with respect to the adapter assembly 200. In addition, the gear elements 570 and 572 provide for a gearing reduction due to a worm gear/worm wheel drive relationship, thereby obviating the need for additional gear reduction mechanisms at the proximal end of the adapter assembly 200.

Figure 28:
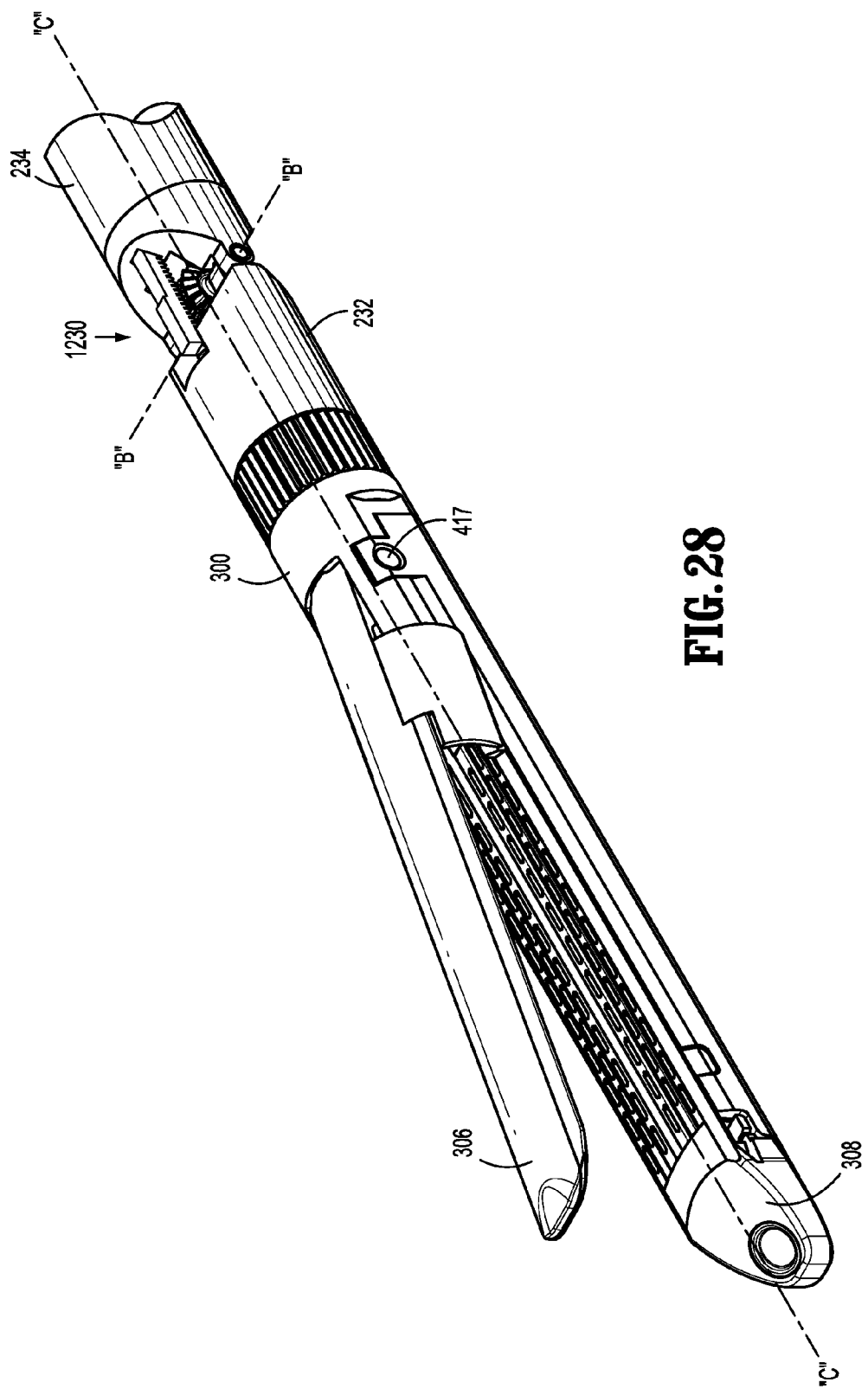
FIG. 28 is a perspective view of another embodiment of an articulating neck assembly with an end effector connected to a distal end of the adapter assembly of FIG. 1, oriented in a linear, non-articulated orientation, according to the present disclosure.
Figure 29:
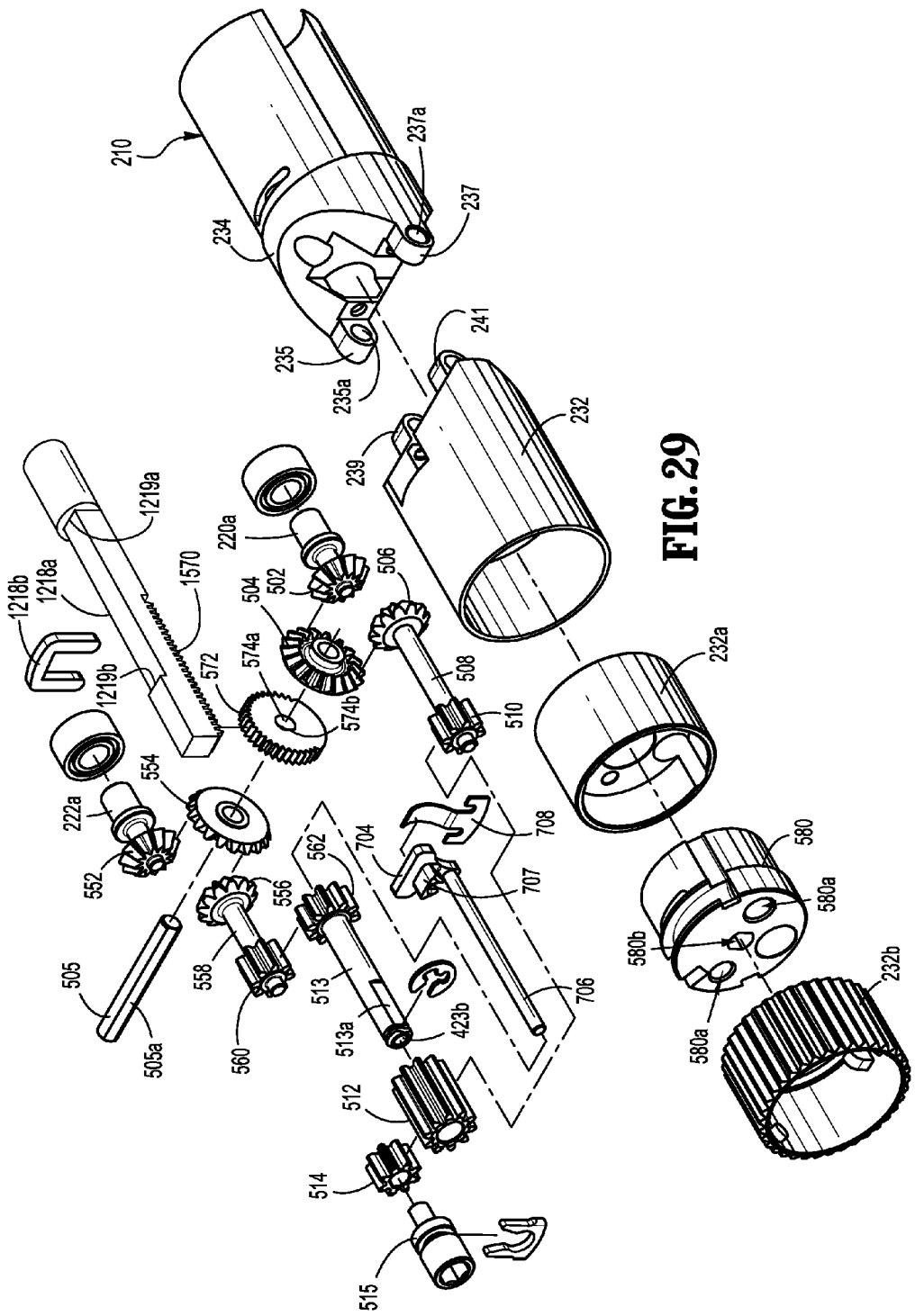
FIG. 29 is a perspective, disassembled view of the articulating neck assembly of FIG. 28 according to the present disclosure.
Figure 30:
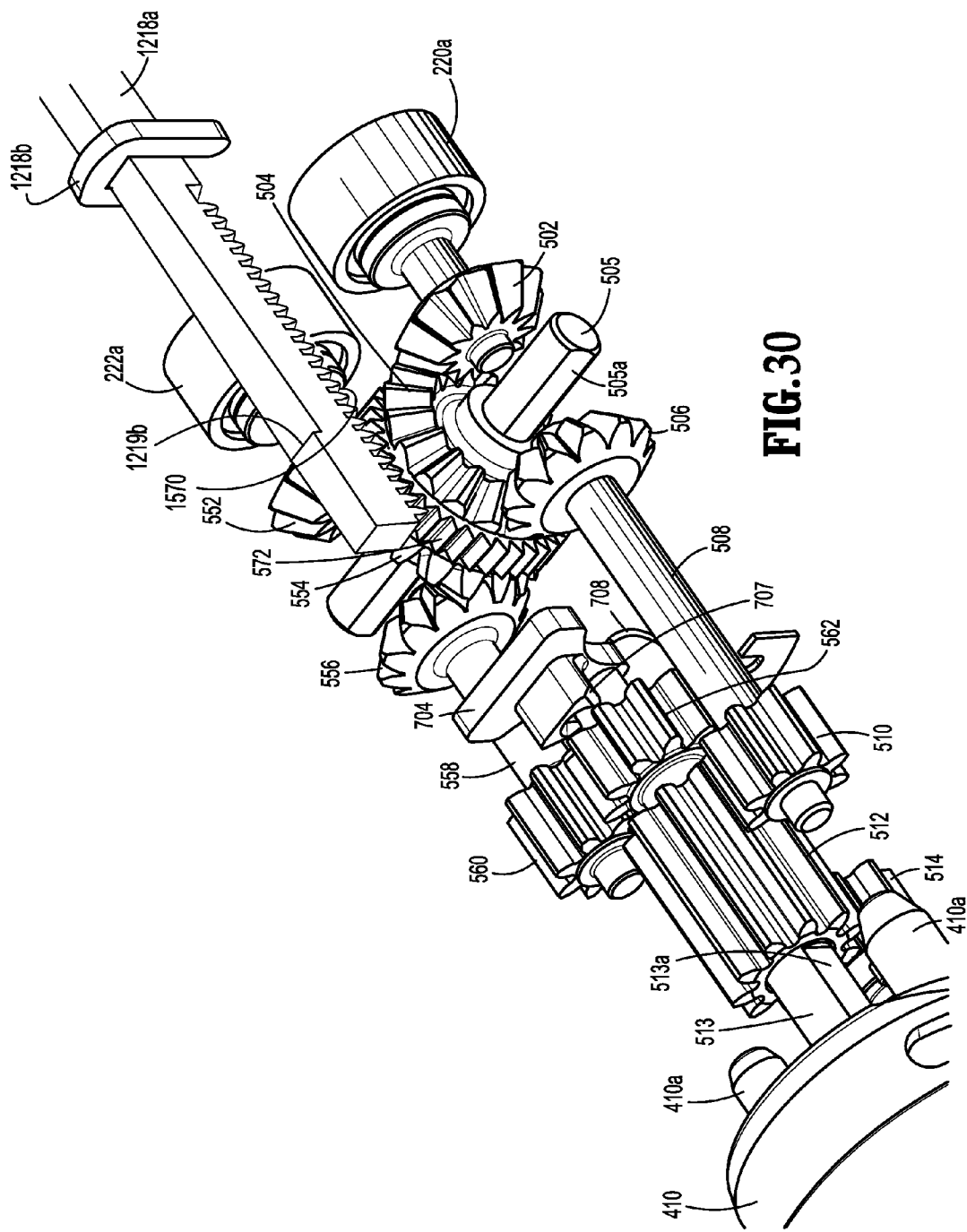
FIG. 30 is a top perspective, partially-disassembled view of the articulating neck assembly of FIG. 28 according to the present disclosure.

Referring to FIGS. 28-30, another embodiment of an articulating assembly 1230 provided in accordance with the present disclosure including a longitudinally translating drive shaft 1218a. Articulating assembly 1230 is substantially similar to articulating assembly 230 and includes most of the components of articulating assembly 230, which are not described below to avoid repetition. Drive shaft 1218a is operatively disposed within body portion 210. Drive shaft 1218a includes a first gear element 1570 that engages pivoting gear element 572. In embodiments, gear element 1570 may be configured as a toothed rack that engages pivoting gear element 572 in a rack and pinion relationship, as best illustrated in FIG. 30.

Figure 31:
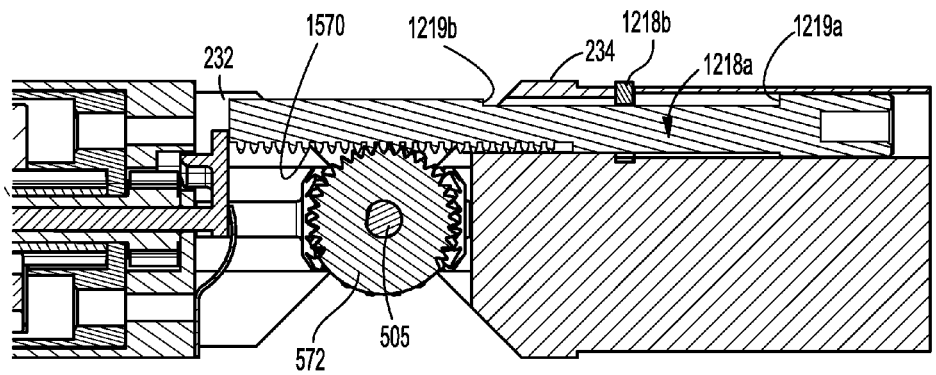
FIG. 31 is a cross-sectional, side view of the end effector connected to the articulating neck assembly of FIG. 28 oriented in a linear, non-articulated orientation, according to the present disclosure.
Figure 32:
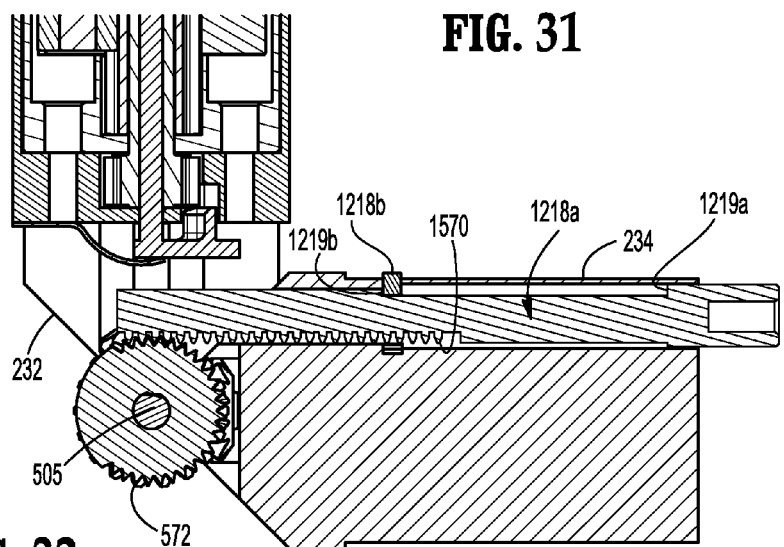
FIG. 32 is a cross-sectional, side view of the end effector connected to the articulating neck assembly of FIG. 28 oriented in a first articulated orientation, according to the present disclosure.
Figure 33:
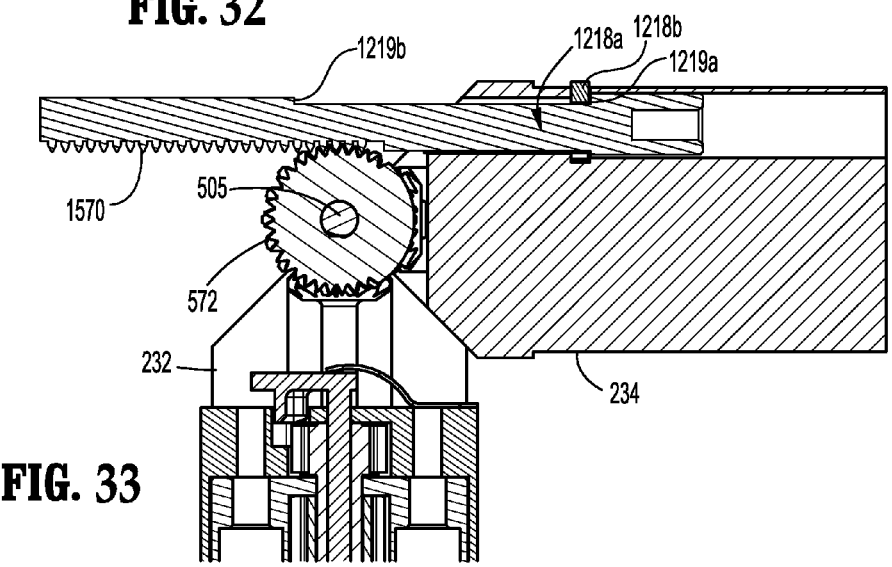
FIG. 33 is a cross-sectional, side view of the end effector connected to the articulating neck assembly of FIG. 28 oriented in a second articulated orientation, according to the present disclosure.

With reference to FIGS. 31-33, articulation of joint member 232 about articulation axis "B-B" (FIG. 28) is imparted by longitudinal translation of drive shaft 1218a along its longitudinal axis, which is parallel to the longitudinal axis "A-A" (FIG. 10). Longitudinal movement of drive shaft 1218a, in turn, rotates pivoting gear element 572 via first gear element 1570. The longitudinal translation of drive shaft 1218a may be accomplished via a drive mechanism described above with respect to drive shaft 218a. First gear element 1570 may extend along drive shaft 1218a such that a portion of first gear element 1570 is adjacent a proximal end of drive shaft 1218a. Since pivoting gear element 572 is securely coupled to pin 505, rotation of pivoting gear element 572 rotates pin 505 and joint member 232, which is also securely coupled thereto as described above.

Drive shaft 1218a also includes a thrust plate 1218b that acts as a stop member preventing longitudinal translation of drive shaft 1218a beyond certain limits (e.g., a proximal limit 1219a or a distal limit 1219b), which in turn, prevents rotation of joint member 232 and end effector 300 beyond a desired point. In embodiments, joint member 232 may be pivoted about the articulation axis "B-B" to a first and second pivoted positions in either direction from a first aligned position in which the second longitudinal axis "C-C" (FIG. 28) is substantially aligned with the first longitudinal axis "A-A" (FIG. 10). The first and second pivoted positions may be up to about 300°, with about 150° of pivot in either direction from the first aligned position. In further embodiments, joint member 232 may be pivoted about the articulation axis "B-B" up to about 180°, with about 90° of pivot in either direction from the first aligned position.

The gearing relationship between gear elements 1570 and 572 allows for precise pivoting of end effector 300 with respect to adapter assembly 200. In addition, the interaction of gear elements 1570 and 572 may provide for a back drive mechanism that permits external forces exerted on an end effector attached to articulating neck assembly 1230 about the pivot axis to back drive the motor until a solid stop is reached (i.e., thrust plate 1218b reaching proximal or distal limit 1219a, 1219b). The solid stop may correspond to the first or second rotated positions of end effector 300. The back drive mechanism may also include a force multiplier configured to reduce the force exerted on the motor by the back drive mechanism. The force multiplier may be from about 1 to about 40, in embodiments, from about 5 to about 20.

It will be understood that various modifications may be made to the embodiments disclosed herein. For example, surgical instrument 100 and/or end effector 300 need not apply staples but rather may apply two part fasteners as is known in the art. Further, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of preferred embodiments. Those skilled in the art will envision other modifications within the scope and spirit of the claims appended thereto.

What is claimed:

1. A surgical device, comprising:
  a jaw assembly including a first jaw and a second jaw moveable relative to the first jaw;
  an articulating assembly removably coupled to a proximal end of the jaw assembly, the articulating assembly including a distal joint member, a proximal joint member, and a pivot pin fixedly coupled to the distal joint member and rotatably coupled to the proximal joint member, wherein the jaw assembly and the distal joint member define a first longitudinal axis extending between the proximal end of the jaw assembly and a distal end of the distal joint member, and the proximal joint member defines a second longitudinal axis; and
  a drive shaft including a gear element meshingly engaged with a pivoting gear element fixedly coupled to the pivot pin, wherein longitudinal movement of the first drive shaft pivots the jaw assembly relative to the proximal joint member about a pivot axis defined by the pivot pin, the pivot axis being perpendicular to the first and second longitudinal axes.

2. The surgical device according to claim 1, wherein the gear element is a toothed rack and the pivoting gear element is a pinion drive.

3. The surgical device according to claim 1 further comprising an elongated member coupled to the proximal joint member and including the drive shaft.

4. The surgical device according to claim 3 further comprising a handle assembly removably coupled to a proximal end of the elongated member, the handle assembly including at least one motor mechanically coupled to and configured to longitudinally move the drive shaft.

5. The surgical device according to claim 4, wherein the drive shaft is configured to apply a force that back drives the motor in response an external force applied to the articulating assembly about the pivot axis.

6. The surgical device according to claim 1, wherein the drive shaft includes a proximal stop, a distal stop, and a thrust plate positioned between the proximal and distal stops.

7. The surgical device according to claim 6, wherein the proximal stop is positioned along the first drive shaft at a first position corresponding to a first pivoted position of the distal joint member and the distal stop is positioned along the first drive shaft at a second position corresponding to a second pivoted position of the distal joint member.

8. The surgical device according to claim 7, wherein in the first pivoted position, the second longitudinal axis defines a first angle with the first longitudinal axis in a first direction.

9. The surgical device according to claim 8, wherein in the second pivoted position, the second longitudinal axis defines a second angle with the first longitudinal axis in a second direction, the second direction being opposite the first direction.

10. The surgical device according to claim 9, wherein the first and second angles are about 150°.

11. The surgical device according to claim 8, wherein the first and second angles are about 90°.

12. A surgical device, comprising:
- a jaw assembly including a first jaw and a second jaw moveable relative to the first jaw;
- an articulating neck assembly removably coupled to the proximal end of the jaw assembly, the articulating neck assembly including a distal joint member, a proximal joint member, a pivot pin fixedly coupled to the distal joint member and rotatably coupled to the proximal joint member, and a first gear element fixedly coupled to the pivot pin, wherein the jaw assembly and the distal joint member define a first longitudinal axis extending between a proximal end of the jaw assembly and a distal end of the distal joint member, and the proximal joint member defines a second longitudinal axis;
- a first drive shaft meshingly engaged with the first gear element, wherein longitudinal movement of the first drive shaft pivots the jaw assembly relative to the proximal joint member about a pivot axis defined the pivot pin, the pivot axis being perpendicular to the first and second longitudinal axes;
- a second drive shaft coupled to the jaw assembly, wherein rotation of the second drive shaft moves the second jaw relative to the first jaw; and
- a third drive shaft coupled to the jaw assembly, wherein rotation of the third drive shaft rotates the jaw assembly about the first longitudinal axis.

13. The surgical device according to claim 12, wherein the first gear element is a toothed rack and the pivoting gear element is a pinion drive.

14. The surgical device according to claim 12 further comprising an elongated member coupled to the proximal joint member and including the first drive shaft.

15. The surgical device according to claim 14 further comprising a handle assembly removably coupled to a proximal end of the elongated member, the handle assembly including at least one motor mechanically coupled to and configured to longitudinally move the first drive shaft.

16. The surgical device according to claim 15, wherein the first drive shaft applies a force that back drives the motor when an external force is applied to the articulating assembly about the pivot axis.

17. The surgical device according to claim 16, wherein the first drive shaft includes a proximal stop, a distal stop, and a thrust plate positioned between the proximal and distal stops.

18. The surgical device according to claim 17, wherein the proximal stop is positioned along the first drive shaft at a first position corresponding to a first pivoted position of the distal joint member and the distal stop is positioned along the first drive shaft at a second position corresponding to a second pivoted position of the distal joint member.

19. The surgical device according to claim 18, wherein in the first pivoted position, the second longitudinal axis defines a first angle with the first longitudinal axis in a first direction and in the second pivoted position, the second longitudinal axis defines a second angle with the first longitudinal axis in a second direction, the second direction being opposite the first direction.

* * * * *